US010294471B2

(12) United States Patent
Lin et al.

(10) Patent No.: US 10,294,471 B2
(45) Date of Patent: May 21, 2019

(54) METHOD OF ISOLATING APTAMERS FOR MINIMAL RESIDUAL DISEASE DETECTION

(71) Applicant: THE TRUSTEES OF COLUMBIA UNIVERSITY IN THE CITY OF NEW YORK, New York, NY (US)

(72) Inventors: Qiao Lin, New York, NY (US); Milan N. Stojanovic, Ridgewood, NJ (US); Timothy R. Olsen, New York, NY (US); Tilla S. Worgall, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/414,376

(22) Filed: Jan. 24, 2017

(65) Prior Publication Data

US 2017/0130218 A1    May 11, 2017

Related U.S. Application Data

(63) Continuation of application No. PCT/US2015/043824, filed on Aug. 5, 2015.

(60) Provisional application No. 62/033,574, filed on Aug. 5, 2014.

(51) Int. Cl.
*C07H 21/04* (2006.01)
*C12N 15/10* (2006.01)
*C12N 15/115* (2010.01)

(52) U.S. Cl.
CPC ............ *C12N 15/10* (2013.01); *C12N 15/115* (2013.01); *C12N 2310/16* (2013.01); *C12N 2320/11* (2013.01); *C12N 2330/31* (2013.01)

(58) Field of Classification Search
CPC ...................................................... C12Q 1/68
See application file for complete search history.

(56) References Cited

U.S. PATENT DOCUMENTS

| | | | |
|---|---|---|---|
| 4,979,509 A | 12/1990 | Hakky | |
| 5,508,164 A | 4/1996 | Kausch et al. | |
| 5,649,947 A | 7/1997 | Auerbach et al. | |
| 5,968,820 A | 10/1999 | Zborowski et al. | |
| 5,998,588 A | 12/1999 | Hoffman et al. | |
| 6,016,686 A | 1/2000 | Thundat | |
| 6,132,580 A | 10/2000 | Mathies et al. | |
| 6,210,326 B1 | 4/2001 | Ehwald | |
| 6,221,677 B1 | 4/2001 | Wu et al. | |
| 6,344,326 B1 | 2/2002 | Nelson et al. | |
| 6,395,165 B2 | 5/2002 | Bulan et al. | |
| 6,397,661 B1 | 6/2002 | Grimes et al. | |
| 6,432,290 B1 | 8/2002 | Harrison et al. | |
| 6,479,242 B1 | 11/2002 | Gou et al. | |
| 6,514,718 B2 | 2/2003 | Heller et al. | |
| 6,641,783 B1 | 11/2003 | Pidgeon et al. | |
| 6,837,896 B2 | 1/2005 | Matsutani et al. | |
| 6,887,693 B2 | 5/2005 | McMillan et al. | |
| 6,933,114 B2 | 8/2005 | Lupold et al. | |
| 7,029,852 B2 | 4/2006 | Liebholz et al. | |
| 7,074,637 B2 | 7/2006 | Lutz et al. | |
| 7,141,375 B2 | 11/2006 | Pietras et al. | |
| 7,151,167 B2 | 12/2006 | Gjerde et al. | |
| 7,217,542 B2 | 5/2007 | Tyvoll et al. | |
| 7,256,695 B2 | 8/2007 | Hamel et al. | |
| 7,285,412 B2 | 10/2007 | Casagrande et al. | |
| 7,287,415 B2 | 10/2007 | Borwick, III et al. | |
| 7,338,762 B2 | 3/2008 | Gorenstein et al. | |
| 7,413,712 B2 | 8/2008 | Liu et al. | |
| 7,499,738 B2 | 3/2009 | Gerber et al. | |
| 7,704,704 B2 | 4/2010 | Ibey et al. | |
| 7,741,123 B2 | 6/2010 | Pease et al. | |
| 7,887,753 B2 | 2/2011 | Quake et al. | |
| 7,896,809 B2 | 3/2011 | Simpson et al. | |
| 7,932,034 B2 | 4/2011 | Esfandyarpour et al. | |
| 7,964,356 B2 | 6/2011 | Zichi et al. | |
| 8,003,397 B2 | 8/2011 | Wang et al. | |
| 8,124,015 B2 | 2/2012 | Diercks et al. | |
| 9,250,169 B2 | 2/2016 | Ju | |
| 2002/0039783 A1 | 4/2002 | McMillan et al. | |
| 2002/0064780 A1 | 5/2002 | Gold et al. | |

(Continued)

FOREIGN PATENT DOCUMENTS

| EP | 1 903 338 A2 | 3/2008 |
|---|---|---|
| EP | 2 138 587 A1 | 12/2009 |

(Continued)

OTHER PUBLICATIONS

U.S. Appl. No. 12/568,651 (US 2010/0151465), filed Sep. 28, 2009 (Jun. 17, 2010) Jingyue Ju, et al.
U.S. Appl. No. 12/764,898 (U.S. Pat. No. 9,090,663), filed Apr. 21, 2010 (Jul. 28, 2015) Qiao Lin, et al.
U.S. Appl. No. 13/246,404 (U.S. Pat. No. 9,400,233), filed Sep. 27, 2011 (Jul. 26, 2016) Qiao Lin, et al.
U.S. Appl. No. 13/652,214 (U.S. Pat. No. 9,250,169), filed Oct. 15, 2012 (Feb. 2, 2016) Jingyue Ju, et al.
U.S. Appl. No. 14/160,092 (U.S. Pat. No. 9,364,174), filed Jan. 21, 2014 (Jun. 14, 2016) Qiao Lin, et al.
U.S. Appl. No. 14/221,596 (US 2014/0295424), filed Mar. 21, 2014 (Oct. 2, 2014) Qiao Lin, et al.

(Continued)

*Primary Examiner* — Kimberly Chong
(74) *Attorney, Agent, or Firm* — Baker Botts L.L.P.

(57) ABSTRACT

A method for selecting and isolating aptamers that target M-Ig proteins with a microdevice including at least a first selection chamber is provided. The method includes preparing a first sample of M-Ig proteins from a serum; placing the M-Ig proteins in the first selection chamber; introducing a first group of oligomers including at least an M-Ig targeting oligomer into the first selection chamber, whereby the M-Ig targeting oligomer binds to the first sample of M-Ig proteins. The method further includes removing unbound oligomers of the first sample from the first selection chamber to isolate the M-Ig targeting oligomer.

9 Claims, 11 Drawing Sheets

(56) References Cited

U.S. PATENT DOCUMENTS

| | | |
|---|---|---|
| 2002/0099375 A1 | 7/2002 | Hess et al. |
| 2003/0022370 A1 | 1/2003 | Casagrande et al. |
| 2003/0233827 A1 | 12/2003 | Kuo et al. |
| 2004/0005582 A1 | 1/2004 | Shipwash |
| 2004/0043509 A1 | 3/2004 | Stahler et al. |
| 2004/0073100 A1 | 4/2004 | Ballerstadt et al. |
| 2004/0126890 A1 | 7/2004 | Gjerde et al. |
| 2004/0241718 A1 | 12/2004 | McGown |
| 2005/0029236 A1 | 2/2005 | Gambino et al. |
| 2005/0069910 A1 | 3/2005 | Turner et al. |
| 2005/0142582 A1 | 6/2005 | Doyle et al. |
| 2005/0161669 A1 | 7/2005 | Jovanovich et al. |
| 2005/0208487 A1 | 9/2005 | Burmeister et al. |
| 2005/0250117 A1 | 11/2005 | Su et al. |
| 2005/0262943 A1 | 12/2005 | Claydon et al. |
| 2006/0172429 A1 | 8/2006 | Nilsson et al. |
| 2006/0205061 A1 | 9/2006 | Roukes et al. |
| 2006/0207891 A1 | 9/2006 | Althaus et al. |
| 2007/0122811 A1 | 5/2007 | Buzby |
| 2007/0132043 A1 | 6/2007 | Bradley et al. |
| 2007/0184456 A1 | 8/2007 | Chee et al. |
| 2007/0202525 A1 | 8/2007 | Quake et al. |
| 2007/0248958 A1 | 10/2007 | Jovanovich et al. |
| 2007/0292397 A1 | 12/2007 | McNulty et al. |
| 2008/0004905 A1 | 1/2008 | Jung et al. |
| 2008/0014576 A1 | 1/2008 | Jovanovich et al. |
| 2008/0056946 A1 | 3/2008 | Ahmad |
| 2008/0132188 A1 | 6/2008 | Nivio et al. |
| 2008/0182759 A1 | 7/2008 | West et al. |
| 2008/0245971 A1 | 10/2008 | Wimberger-Friedl et al. |
| 2008/0264842 A1 | 10/2008 | Hukari et al. |
| 2009/0011451 A1 | 1/2009 | Rodriguez et al. |
| 2009/0047297 A1 | 2/2009 | Kim et al. |
| 2009/0048124 A1 | 2/2009 | Leamon et al. |
| 2009/0117549 A1 | 5/2009 | Tan et al. |
| 2009/0166196 A1 | 7/2009 | Kayyem |
| 2009/0191642 A1 | 7/2009 | Wang et al. |
| 2009/0227044 A1 | 9/2009 | Dosev et al. |
| 2009/0253181 A1 | 10/2009 | Vangbo et al. |
| 2010/0151465 A1 | 6/2010 | Ju et al. |
| 2010/0203529 A1 | 8/2010 | Kuslich et al. |
| 2010/0255471 A1 | 10/2010 | Clarke et al. |
| 2010/0279283 A1 | 11/2010 | Raghunath et al. |
| 2010/0297733 A1 | 11/2010 | Lin et al. |
| 2011/0143949 A1 | 6/2011 | Heid et al. |
| 2012/0028811 A1* | 2/2012 | Craighead ......... B01L 3/502753 506/1 |
| 2012/0043203 A1 | 2/2012 | Lin et al. |
| 2012/0100521 A1 | 4/2012 | Soper et al. |
| 2012/0142088 A1 | 6/2012 | Hsiao et al. |
| 2012/0263733 A1 | 10/2012 | Lillard, Jr. |
| 2012/0264155 A1 | 10/2012 | Frandsen et al. |
| 2013/0035630 A1 | 2/2013 | Chen |
| 2013/0164755 A1 | 6/2013 | Weng et al. |
| 2013/0274113 A1 | 10/2013 | Kim et al. |
| 2014/0038301 A1 | 2/2014 | Ju et al. |
| 2014/0248621 A1 | 9/2014 | Collins |
| 2017/0067091 A1 | 3/2017 | Lin et al. |

FOREIGN PATENT DOCUMENTS

| | | |
|---|---|---|
| KR | 10-2009-0032457 | 4/2009 |
| WO | WO 2005/021725 A2 | 3/2005 |
| WO | WO 2006/021410 A1 | 3/2006 |
| WO | WO 2007/092713 A2 | 8/2007 |
| WO | WO 2007/111639 A1 | 10/2007 |
| WO | WO 2008/042481 A2 | 4/2008 |
| WO | WO 2008/092213 A1 | 8/2008 |
| WO | WO 2009/140326 A2 | 11/2009 |
| WO | WO 2010/073020 A1 | 7/2010 |
| WO | WO 2010/091400 A2 | 8/2010 |
| WO | WO 2010/123521 A1 | 10/2010 |
| WO | WO 2010/141921 A1 | 12/2010 |
| WO | WO 2012/162779 A1 | 12/2012 |
| WO | WO 2013/044217 A1 | 3/2013 |
| WO | WO 2013/044240 A1 | 3/2013 |
| WO | WO 2014/018688 A2 | 1/2014 |
| WO | WO 2014/078521 A1 | 5/2014 |
| WO | WO 2014/086956 A2 | 6/2014 |

OTHER PUBLICATIONS

U.S. Appl. No. 14/223,767 (US 2014/0296095), filed Mar. 24, 2014 (Oct. 2, 2014) Qiao Lin, et al.
U.S. Appl. No. 14/743,303 (US 2016/0146797), filed Jun. 18, 2015 (May 26, 2016) Qiao Lin, et al.
U.S. Appl. No. 14/978,716 (US 2016/0169780), filed Dec. 22, 2015 (Jun. 16, 2016) Jingyue Ju, et al.
U.S. Appl. No. 15/153,813 (US 2016/0249837), filed May 13, 2016 (Sep. 1, 2016) Qiao Lin, et al.
U.S. Appl. No. 15/269,494 (US 2017/0067091), filed Sep. 19, 2016 (Mar. 9, 2017) Qiao Lin, et al.
U.S. Appl. No. 12/568,651, Dec. 31, 2012 Notice of Abandonment.
U.S. Appl. No. 12/568,651, Apr. 13, 2012 Final Office Action.
U.S. Appl. No. 12/568,651, Mar. 12, 2012 Response to Non-Final Office Action.
U.S. Appl. No. 12/568,651, Sep. 12, 2011 Non-Final Office Action.
U.S. Appl. No. 12/568,651, Aug. 1, 2011 Response to Restriction Requirement.
U.S. Appl. No. 12/568,651, May 5, 2011 Restriction Requirement Filed.
U.S. Appl. No. 12/764,898, Jul. 21, 2014 Non-Final Office Action.
U.S. Appl. No. 12/764,898, Apr. 29, 2013 Amendment and Request for Continued Examination (RCE).
U.S. Appl. No. 12/764,898, Nov. 28, 2012 Final Office Action.
U.S. Appl. No. 12/764,898, Sep. 5, 2012 Response to Non-Final Office Action.
U.S. Appl. No. 12/764,898, Jun. 5, 2012 Non-Final Office Action.
U.S. Appl. No. 12/764,898, Jul. 23, 2015 Applicant Initiated Interview Summary.
U.S. Appl. No. 12/764,898, Jun. 23, 2015 Issue Fee Payment.
U.S. Appl. No. 12/764,898, Mar. 26, 2015 Notice of Allowance.
U.S. Appl. No. 12/764,898, Jan. 23, 2015 Applicant Initiated Interview Summary.
U.S. Appl. No. 12/764,898, Jan. 21, 2015 Response to Non-Final Office Action.
U.S. Appl. No. 13/246,404, Jun. 22, 2016 Issue Fee Payment.
U.S. Appl. No. 13/246,404, Mar. 28, 2016 Notice of Allowance.
U.S. Appl. No. 13/246,404, Feb. 25, 2016 Response to Non-Final Office Action.
U.S. Appl. No. 13/246,404, Feb. 11, 2016 Applicant Initiated Interview Summary.
U.S. Appl. No. 13/246,404, Sep. 25, 2015 Non-Final Office Action.
U.S. Appl. No. 13/246,404, Sep. 17, 2015 Response to Restriction Requirement.
U.S. Appl. No. 13/246,404, Mar. 26, 2015 Restriction Requirement Filed.
U.S. Appl. No. 13/246,404, Jun. 27, 2014 Amendment and Request for Continued Examination (RCE).
U.S. Appl. No. 13/246,404, Jan. 30, 2014 Final Office Action.
U.S. Appl. No. 13/246,404, Oct. 18, 2013 Response to Non-Final Office Action.
U.S. Appl. No. 13/246,404, May 23, 2013 Non-Final Office Action.
U.S. Appl. No. 13/652,214, May 28, 2014 Non-Final Office Action.
U.S. Appl. No. 13/652,214, Dec. 17, 2015 Issue Fee Payment.
U.S. Appl. No. 13/652,214, Sep. 18, 2015 Notice of Allowance.
U.S. Appl. No. 13/652,214, Jun. 22, 2015 Amendment and Request for Continued Examination (RCE).
U.S. Appl. No. 13/652,214, Jun. 16, 2015 Applicant Initiated Interview Summary.
U.S. Appl. No. 13/652,214, Dec. 22, 2014 Final Office Action.
U.S. Appl. No. 13/652,214, Nov. 24, 2014 Response to Non-Final Office Action.
U.S. Appl. No. 13/652,214, Apr. 7, 2014 Response to Restriction Requirement.

(56) References Cited

OTHER PUBLICATIONS

U.S. Appl. No. 13/652,214, Feb. 6, 2014 Restriction Requirement Filed.
U.S. Appl. No. 14/160,092, May 13, 2016 Issue Fee Payment.
U.S. Appl. No. 14/160,092, Apr. 12, 2016 Notice of Allowance.
U.S. Appl. No. 14/160,092, Mar. 24, 2016 Response to Non-Final Office Action.
U.S. Appl. No. 14/160,092, Feb. 19, 2016 Notice of Allowance.
U.S. Appl. No. 14/160,092, Jan. 15, 2016 Response to Non-Final Office Action.
U.S. Appl. No. 14/160,092, Sep. 3, 2015 Non-Final Office Action.
U.S. Appl. No. 14/160,092, Jun. 30, 2015 Response to Restriction Requirement.
U.S. Appl. No. 14/160,092, Mar. 3, 2015 Restriction Requirement Filed.
U.S. Appl. No. 14/221,596, Jan. 18, 2017 Applicant Initiated Interview Summary.
U.S. Appl. No. 14/221,596, Apr. 21, 2017 Non-Final Office Action.
U.S. Appl. No. 14/221,596, Mar. 30, 2017 Amendment and Request for Continued Examination (Rce).
U.S. Appl. No. 14/221,596, Jan. 30, 2017 Notice of Appeal Filed.
U.S. Appl. No. 14/221,596, Jan. 22, 2016 Non-Final Office Action.
U.S. Appl. No. 14/221,596, Jan. 4, 2016 Response to Restriction Requirement.
U.S. Appl. No. 14/221,596, Aug. 17, 2015 Restriction Requirement Filed.
U.S. Appl. No. 14/221,596, Jul. 29, 2016 Final Office Action.
U.S. Appl. No. 14/221,596, May 6, 2016 Response to Non-Final Office Action.
U.S. Appl. No. 14/223,767, Mar. 10, 2017 Non-Final Office Action.
U.S. Appl. No. 14/223,767, Feb. 15, 2017 Amendment and Request for Continued Examination (Rce).
U.S. Appl. No. 14/223,767, Aug. 17, 2016 Final Office Action.
U.S. Appl. No. 14/223,767, May 6, 2016 Response to Non-Final Office Action.
U.S. Appl. No. 14/223,767, Jan. 13, 2016 Applicant Initiated Interview Summary.
U.S. Appl. No. 14/223,767 Sep. 11, 2015 Non-Final Office Action.
U.S. Appl. No. 14/743,303, Apr. 12, 2017 Non-Final Office Action.
U.S. Appl. No. 14/743,303, Mar. 1, 2017 Response to Restriction Requirement.
U.S. Appl. No. 14/743,303, Sep. 2, 2016 Restriction Requirement Filed.
AAAT Bioquest, "Classic reactive flourescent labeling dyes & their applications," AAT Bioquest, Inc. Product Technical Information Sheet, 2010 [online]. Retrieved on Jan. 29, 2013 at http://www.biomol.de.details/AB/Classic_Reactive_Flourescent_Labeling_Dyes.pdf>.
Adams, et al., "Multitarget Magnetic Activated Cell Sorter," Proceedings of the National Academy of Sciences of the United States of America, 105:18165-18170 (2008).
Ahn et al., "A sol-gel-based microfluidics system enhances the efficiency of RNA aptamer selection," Oligonucleotides, 21(2):93-100 (2011).
Barnes et al., "A femtojoule calorimeter using micromechanical sensors," AIP: Review of Scientific Instruments 65:3793-3798 (Dec. 1994).
Berger, et al., "Design of a Microfabricated Magnetic Cell Separator," Electrophoresis, 22:3883-3892 (2001).
Blazej, et al., "Microfabricated bioprocessor for integrated nanoliter-scale Sanger DNA sequencing," PNAS, 103(19):7240-7245 (2006).
Bock, et al., "Selection of single-stranded-DNA molecules that bind and inhibit human thrombin," Nature, 355:564-566 (1992).
Brody, et al., "The use if aptamers in large arrays for molecular diagnostics," Molecular Diagnosis, 4(4):381-388 (1999).
Broyles, et al., "Sample filtration, concentration, and separation integrated on microfluidic devices," Anal. Chemistry, 75:2761-2767 (2003).
Bruno, "Predicting the Uncertain Future of Aptamer-Based Diagnostics and Therapeutics," Molecules 20:6866-6887 (2015).
Burgstaller, et al., "Aptamers as tools for target prioritization and lead identification," Drug Discovery Today, 7(24):1221-1228 (2002).
Cavicchi et al., "Micro-differential scanning calorimeter for combustible gas sensing," Sensors and Actuators B; Chemical 97(1):22-30 (Jan. 2004).
Chang, et al., "Electrokinetic Mixing in Microfluidic Systems," Microfluidics and Nanofluidics, 3:501-525 (2007).
Chen et al., "An automatic microfluidic system that continuously performs the systematic evolution of ligands by exponential enrichment," Microfluidics and Nanofluidics, 13(6):929-939 (2012).
Chen, et al., "Total nucleic acid analysis integrated on microfluidic devices," Lab on a Chip, 7(11):1413-1423 (2007).
Cho, et al., "PDMS-glass serpentine microchannel chip for time domain PCR with bubble suppression in sample injection," Journal of Micromechanics and Microengineering, 17(9):1810-1817 (2007).
Chou, et al., "A microfabricated device for sizing and sorting DNA molecules," PNAS, 96(1):11-13 (1999).
Collett, et al., "Functional RNA microarrays for high-throughput screening of antiprotein aptamers," Analytical Biochemistry, 338(1):113-123 (2005).
Cox, et al., "Automated selection of anti-protein aptamers," Bioorganic & Medicinal Chemistry, 9(10):2525-2531 (2001).
D'Orazio, et al., "Biosensors in clinical chemistry," Clinica Chimica Acta, 334:41-69 (2003).
Dahlin, et al., "Poly(dimethylsiloxane)-based microchip for two-dimensional solid-phase extraction-capillary electrophoresis with an integrated electrospray emitter tip," Analytical Chemistry, 77(16):5356-5363 (2005).
Darby, R., Chemical Engineering Fluid Mechanics, 2nd Edition, Revised and Expanded, (Marcel Dekker, New York, 2001) (Table of Contents).
Deng et al., "Aptamer affinity chromatography for rapid assay of adenosine in microdialysis samples collected in vivo," Journal of Chromatography A, 1005(1-2):123-130 (2003).
Diehl, et al., "BEAMing: single-molecule PCR on microparticles in water-in-oil emulsions," Nature Methods, 3(7):551-559 (2006).
Dittmer, et al., "A DNA-based machine that can cyclically bind and release thrombin," Angewandte Chemie-International Edition, 43(27):3550-3553 (2004).
Doherty, et al., "Sparsely cross-linked "nanogel" matrixes as fluid, mechanically stabilized polymer networks for high-throughput microchannel DNA sequencing," Anal. Chem., 76:5249-5256 (2004).
Drabovich, et al., "Selection of smart aptamers by equilibrium capillary electrophoresis of equilibrium mixtures (ECEEM)," Journal of the American Chemical Society, 127(32):11224-11225 (2005).
Drabovich, et al., "Selection of smart aptamers by methods of kinetic capillary electrophoresis," Anal. Chem., 78(9):3171-3178 (2006).
Dua et al., "Patents on SELEX and Therapeutic Aptamers," Recent Patents on DNA & Gene Sequences 2:172-186 (2008).
Earhart, et al., "Microfabricated magnetic sifter for high-throughput and high-gradient magnetic separation," Journal of Magnetism and Magnetic Materials, 321:1436-1439 (2009).
El-Ali, et al., "Cell stimulus and lysis in a microfluidic device with segmented gas-liquid flow," Analytical Chemistry, 77(11):3629-3636 (2005).
Espy, et al., "An Instrument for Sorting of Magnetic Microparticles in a Magnetic Field Gradient," Cytometry Part A, 69A:1132-1142 (2006).
Estes, et al., "On Chip Cell Separator Using Magnetic Bead-Based Enrichment and Depletion of Various Surface Markers," Biomedical Microdevices, 11:509-515 (2009).
Farokhzad, et al., "Targeted nanoparticle-aptamer bioconjugates for cancer chemotherapy in vivo," PNAS, 103(16):6315-6320 (2006).
Fivash, et al., "BIAcore for macromolecular interaction," Current Opinion on Biotechnology, 9(1):97-101 (1998).
Furdui, et al., "Immunomagnetic T cell capture from blood for per analysis using microfluidic systems," Lab on a Chip, 4:614-618 (2004).
Geiger, et al., "RNA aptamers that bind L-arginine with sub-micromolar dissociation constants and high enantioselectivity," Nucleic Acids Research, 24(6):1029-1036 (1996).

(56) References Cited

OTHER PUBLICATIONS

Giordano, et al., "Towards dynamic coating of glass microchip chambers for amplifying DNA via the polymerase chain reaction," Electrophoresis, 22(2):334-340 (2001).
Gopinath, S.C.B., "Methods developed for SELEX," Analytical and Bioanalytical Chemistry, 387(1):171-182 (2007).
Green, et al., "Aptamers as reagents for high-throughput screening," BioTechniques, 30(5):1094-1110 (2001).
Hamula, et al., "Selection and analytical applications of aptamers," Trends Anal. Chem., 25(7):681-691 (2006).
Handbook of Affinity Chromatography, 2 Edition. Edited by David S. Hage, Taylor and Francis, (Table of Contents) (2006).
Herr, et al., "Aptamer-conjugated nanoparticles for selective collection and detection of cancer cells," Analytical Chemistry, 78(9):2918-2924 (2006).
Hessel, et al., "Micromixers—a Review on Passive and Active Mixing Principles," Chemical Engineering Science, 60:2479-2501 (2005).
Hoffman, et al., "Immobilized DNA aptamers used as potent attractors for porcine endothelial precursor cells," Journal of Biomedical Materials Research Part A, 84A(3):614-621 (2008).
Hsing, et al., "Mirco- and nano-magnetic particles for applications in biosensing," Electroanalysis, 10(7-8):755-768 (2007).
Huang et al., "A biocompatible affinity MEMS sensor for continuous monitoring of glucose," IEEE 4th International Nano/Micro Engineered and Molecular Systems, Shenzhen, China, pp. 797-802 (2009).
Huang et al., "A Capacitive MEMS viscometric sensor for affinity detection of glucose," Microelectromechanical System 18(6):1246-1254 (2009).
Huang et al., "A capacitively based MEMS affinity glucose sensor," IEEE SolidState Sensors, Actuators and Microsystems Conference, Denver, Colorado, pp. 1457-1460 (2009).
Huang et al., "A MEMS affinity glucose sensor using a biocompatible glucose-responsive polymer," Sensors and Actuators B: Chemical 140(2):603-609 (2009).
Huang et al., "A MEMS differential affinity sensor for continuous glucose detection," Soli-state Sensors, Actuators and Microsystems Conference, (abstract only) Jun. 5-9, 2011.
Huang et al., "A MEMS sensor for continuous monitoring of glucose on subcutaneous tissue," IEEE 22nd International Conference on Microelectromechanical Systems (MEMS), Sorrento, Italy, pp. 352-355 (2009).
Huang, et al., Integrated microfluidic system for rapid screening of CRP aptamers utilizing systematic evolution of ligands by exponential enrichment (SELEX), Biosensors and Bioelectronics, 25(17):1761-1766 (2010).
Hybarger, et al., "A microfluic SELEX prototype," Analytical and Bioanalytical Chemistry, 384(1):191-198 (2006).
Inglis, et al., "Continuous Microfluidic Immunomagnetic Cell Separation," Applied Physics Letters, 85(21):5093-5095 (2004).
Inokuchi et al., "Development of micro immuno-magnetic cell sorting system with lamination mixer and magnetic separator" Proc. 25th Sensor Symp., 2008, pp. 1-2.
International Search Report and Written Opinion for PCT/US2009/062891, dated Jan. 13, 2010.
International Search Report and Written Opinion for PCT/US2012/048819, dated Nov. 15, 2012.
International Search Report and Written Opinion for PCT/US2012/056888, dated Feb. 25, 2013.
International Search Report and Written Opinion for PCT/US2012/056926, dated Dec. 3, 2012.
International Search Report and Written Opinion for PCT/US2013/070075, dated Feb. 21, 2014.
International Search Report and Written Opinion dated Jun. 22, 2015 in International Application No. PCT/US2015/022044.
International Search Report dated Nov. 10, 2015 in International Application No. PCT/US15/43824.
International Search Report for PCT/US2008/058433, dated Jun. 30, 2008.

James, W., "Aptamers in the virologists' toolkit," Journal of General Virology, 88(8):351-364 (2007).
Jayasena, "Aptamers: An emerging class of molecules that rival antibodies in diagnostics," Clinical Chemistry, 45(9):1628-1650 (1999).
Jellinek, et al., "Potent 2'-amino-2'-deoxypyrimidine RNA inhibitors of basic fibroblast growth-factor," Biochemistry, 34(36):11363-11372 (1995).
Jenison, et al., "High-resolution molecular discrimination by RNA," Science, 263(5152):1425-1429 (1994).
Jensen, et al., "Kinetics for hybridization of peptide nucleic acids (PNA) with DNA and RNA studied with the BIAcore technique," Biochemistry, 36(16):5072-5077 (1997).
Kanter, et al., "Cell-free production of SCFV fusion proteins: an efficient approach for personalized lymphoma vaccines," Blood, 109(8):3393-3399 (2007).
Kim et al., "A microchip for nucleic acid isolation and enrichment," 2012 IEEE 25th International Conference on Micro Electro Mechanical Systems, pp. 765-768 (2012).
Kim et al., "Nucleic acid isolation and enrichment on a microchip," Sensors and Actuators A: Physical 195:183-190 (2013).
Kim, et al., "Solid phase capturable dideoxynucleotides for multiplex genotyping using mass spectrometry," Nucleic Acids Research, 30(16):e85 (2002).
Kopp, et al., "Chemical amplification: Continuous-flow PCR on a chip," Science, 280(5366):1046-1048 (1998).
Kristinsson et al., "Improved long-term survival in multiple myeloma up to the age of 80 years," Leukemia 28:1346-1348 (2014).
Lai et al., "High-speed (104 ° C./s) scanning microcalorimetry with monolayer sensitivity (J/m2)," Applied Physics Letters 67:1229-1231 (Aug. 1995).
Lai et al., "Aptamer-based electrochemical detection of picomolar platelet-derived growth factor directly in blood serum," Analytical Chemistry, 79(1):229-233 (2007).
Lee, et al., "A therapeutic aptamer inhibits angiogenesis by specifically targeting the heparin binding domain of VEGF 165," PNAS, 102(52):18902-18907 (2005).
Lermo, et al., "In-situ DNA amplification with magnetic primers for the electrochemical detection of food pathogens," Biosensors and Bioelectronics, 22(9-10):2010-2017 (2007).
Lien, et al., "Purification and enrichment of virus samples utilizing magnetic beads on a microfluidic system," Lab on a Chip, 7:868-875 (2007).
Lin et al., "Aptamer-Based Microfluidic Biosensors," 9th IEEE Conference on Nanotechnology, pp. 812-814 (2009).
Liu, et al., "Passive Mixing in a Three-Dimensional Serpentine Microchannel," Journal of Microelectromechanical Systems, 9:190-197 (2000).
Liu, et al., "Micro air bubble formation and its control during polymerase chain reaction (PCR) in polydimethylsiloxane (PDMS) microreactos," Journal of Micromechanics and Microengineering, 17:2055-2064 (2007).
Lowe, et al., "Multiplex single nucleotide polymorphism genotyping utilizing ligase detection reaction coupled surface enhanced raman spectroscopy," Analytical Chemistry, 82(13):5810-5814 (2010).
Lund-Olesen, et al., "Capture of DNA in Microfluidic Channel Using Magnetic Beads: Increasing Capture Efficiency with Integrated Microfluidic Mixer," Journal of Magnetism and Magnetic Materials, 311:396-400 (2007).
Lupold, et al., "Identification and characterization of nuclease-stabilized RNA molecules that bind human prostate cancer cells via the prostate-specific membrane antigen," Cancer Research, 62(14):4029-4033 (2002).
Mannironi, et al., "In vitro selection of dopamine RNA ligands," Biochemistry, 36(32):9726-9734 (1997).
Mansouri et al., "A Miniature optical glucose sensor based on affinity binding," Nature Biotechnology 2:885-890 (1984).
Mendonsa, et al., "In-vitro evolution of functional DNA using capillary electrophoresis," Journal of the American Chemical Society, 126(1):20-21 (2004).
Miltenyi, et al., "High gradient magnetic cell separation with MACS," Cytometry Part A., 11(2):231-238 (1990).

(56) References Cited

OTHER PUBLICATIONS

Misra, et al., "Microbead device for isolating biotinylated oligonucleotides for use in mass spectrometric analysis," Analytical Biochemistry, 384(1):96-100 (2009).
Mosing, et al., "Capillary electrophoresis-SELEX selection of aptamers with affinity for HIV-1 reverse transcriptase," Anal. Chem., 77(19):6107-6112 (2005).
Murphy, et al., "An improved method for the in vitro evolution of aptamers and applications in protein detection and purification," Nucleic Acids Research, 31(18):e110 (2003).
Nguyen, et al., "An aptamer-based microfluidic device for thermally controlled affinity extraction," Microfluid Nanofluid, 6(4):479-487 (2009).
Nguyen, et al., "Micromixers—a Review," Journal of Micromechanics and Microengineering, 15:R1-R16 (2005).
Nieuwlandt, et al., "In-vitro selection of RNA ligands to substance-P," Biochemistry, 34(16):5651-5659 (1995).
Nimjee, et al., "The potential of aptamers as anticoagulants," Trends Cardiovascular Medicine, 15(1):41-45 (2005).
O'Sullivan, et al., "Aptasensors—the future of biosensing," Analytical and Bioanalytical Chemistry, 372:44-48 (2002).
Oh, et al., "Screening of Molecular Libraries Using the Continuous-Flow, Micro-Magnetic Cell Sorter," 10th International Conference on Miniaturized Systems for Chemistry and Life Sciences, Nov. 5-9, 2006, Tokyo, Japan, pp. 975-977.
Pamme, et al., "Continuous sorting of magnetic cells via on-chip free-low magnetophoresis," Lab on a Chip, 6(8):974-980 (2006).
Prosek, et al., "Aptamers-basic research, drug development, and clinical applications," Appl. Microbiol. Biotechnol., 69:367-374 (2005).
Ramsey, et al., "Integrated microfluidic device for solid-phase extraction coupled to micellar electrokinetic chromatography separation," Anal. Chem., 77:6664-6670 (2005)..
Ravelet, et al., "Liquid chromatography, electrochromatography, and capillary electrophoresis applications of DNA and RNA aptamers," Journal of Chromatogrraphy A, 1117:1-10 (2006).
Rawstron et al., "Minimal Residual Disease Assessed by Multiparameter Flow Cytometry in Multiple Myeloma: Impact on Outcome in the Medical Research Council Myeloma IX Study," Journal of Clinical Oncology 31:2540-2547 (2013).
Reigstad, et al., "Platelet-derived growth factor (PDGF)-C, a PDGF family member with a vascular endothelial growth factor-like structure," The Journal of Biological Chemistry, 278(19):17114-17120 (2003).
Reuter, et al., "Kinetics of protein-release by an aptamer-based DNA nanodevice," European Physical Journal E., 22(1):33-40 (2007).
Romig, et al., "Aptamer affinity chromatography: combinatorial chemistry applied to protein purification," Journal of Chromatography B-Analytical Technologies in the Biomedical and Life Sciences, 731(2):275-284 (1999).
Sanchez-Freire et al., "Microfluidic single-cell real-time PCR for comparative analysis of gene expression patterns," Nature Protocols, 7:829-838 (Apr. 2012).
Shamah, et al., "Complex target SELEX," Accounts of Chemical Research, 41(1):130-138 (2008).
Shangguan, et al., "Cell-specific aptamer probes for membrane protein elucidation in cancer cells," Journal of Proteome Research, 7(5):2133-2139 (2008).
Shao, et al., "Emulsion PCR: A high efficient way of PCR amplification of random DNA libraries in aptamer selection," PlosOne, 6(9):E24910 (2011).
Shum et al., "Nucleic Acid Aptamers as Potential Therapeutic and Diagnostic Agents for Lymphoma," Journal of Cancer Therapy 4:872-890 (2013).
Sikavitsas, et al., "Transport and kinetic processes underlying biomolecular interactions in the BIACORE optical biosensor," Biotechnology Progress, 18(4):885-897 (2002).
So, et al., "Detection and titer estimation of *Escherichia coli* using aptamer-functionalized single-walled carbon-nanotube field-effect transistors," Small, 4(2):197-201 (2008).
Stahlberg et al., "Single-cell gene-expression profiling and its potential diagnostic applications," Exp. Rev. of Mol. Diagnostics, 11(7):735-740 (Sep. 2011).
Stroock, et al., "Chaotic Mixer for Microchannels," Science, 295:647-651 (2002).
Stroock, et al., "Controlling flows in microchannels with patterned surface charge and topography," Accounts of Chemical Research, 36(8):597-604 (2003).
Supplementary Partial European Search Report dated Aug. 28, 2015 in EP Application No. EP 12834427.
Suzuki et al., "Chaotic mixing of magnetic beads in microcell separator," Proc. 3rd Int. Symp. Turbulence and Shear Flow Phenomena, Jun. 24-27, 2003, pp. 817-822.
Tang, et al., "Chip-based genotyping by mass spectrometry," PNAS, 96(18):10016-10020 (1999).
Tate et al., "Quantitative Serum Free Light Chain Assay—Analytical Issues," The Clinical Biochemist Reviews 30:131-140 (2009).
Taylor, et al., "Dynamics of an anti-VEGF DNA aptamer: A single-molecule study," Biochemical and Biophysical Research Communications, 373(2):213-218 (2008).
Temples, et al., "On-line coupling of size exclusion chromatography and capillary electrophoresis via solid-phase extraction and a Tee-split interface," Journal of Chromatography B, 839:30-35 (2006).
Thorsen, et al., "Microfluidic large-scale integration," Science, 298 (5593):580-584 (2002).
Tombelli et al., "Analytical applications of aptamers," Biosensors and Bioelectronics, 20:2424-2434 (2005).
Toriello et al., "Integrated affinity capture, purification, and capillary electrophoresis microdevice for quantitative double-stranded DNA analysis," Anal. Chem., 79(22):8549-8556 (2007).
Tuerk et al., "Systematic evolution of ligands by exponential enrichment: RNA ligands to bacteriophage T4 DNA polymerase," Science, 249:505-510 (1990).
Unger et al., "Monolithic microfabricated valves and pumps by multilayered soft lithography," Science, 288:113-116 (2000).
Vanden Poel et al., "Performance and calibration of the flash DSC 1, a new, MEMS-based fast scanning calorimeter," Journal of Thermal Analysis and Calorimetry 110(3):1533-1546 (Dec. 2012).
Verpoorte, "Beads and Chips: New Recipes for Analysis," Lab on a Chip, 3:60N-68N (2003).
Viskari et al., "Unconventional detection methods for microfluidic devices," Electrophoresis, 27(9):1797-1810 (2006).
Wallis et al., "Vasopressin is a physiological substrate for the insulin-regulated aminopeptidase IRAP," Am. J. Physiol. Endocrinol. Metab., 293(4):E1092-E1102 (2007).
Wang et al., "A MEMS Isothermal Titration Biocalorimeter," 16th International Conference on Miniaturized Systems for Chemistry and Life Sciences, pp. 195-197 (Oct. 28-Nov. 1, 2012) Okinawa, Japan.
Wang et al., "Demonstration of MEMS-based differential scanning calorimetry for determining thermodynamic properties of biomolecules," Sensors and Actuators B: Chemical, 134:953-958 (2008).
Wang et al., "Pre-binding dynamic range and sensitivity enhancement for immuno-sensor using nanofluidic preconcentrator," Lab on a Chip, 8:392-394 (2007).
White et al., "High-throughput microfluidic single-cell RT-qPCR," PNAS, 108(34):13999-14004 (Aug. 2011).
Williams et al., "Bioactive and nuclease-resistant L-DNA ligand of vasopressin," PNAS, 94(21):11285-11290 (1997).
Wu et al., "MEMS flow sensors for nano-fluidic applications," Sensors and Actuators A., 89(1-2):152-158 (2001).
Xia et al., "Chaotic micromixers using two-layer crossing channels to exhibit fast mixing at low Reynolds numbers," Lab on a Chip, 5(7):748-755 (2005).
Xiaoyu et al., "Polydimethylsiloxane (PDMS)-based spiral channel PCR chip," Electronics Letters, 46(16):890-891 (2005).
Xu et al., "Review: Aptamers in microfluidic chips," Analytica Chimica Acta, 683(1):12-20 (2010).

(56) References Cited

OTHER PUBLICATIONS

Xu et al., "Aptamer-Based Microfluidic Device for Enrichment, Sorting, and Detection of Multiple Cancer Cells," Anal. Chem., 81:7436-7442 (2009).
Yang et al., "Advances in SELEX and application of aptamers in the central nervous system," Biomolecular Engineering, 24(6):583-592 (2007).
Yang et al., "DNA ligands that bind tightly and selectively to cellobiose," PNAS, 95(10):5462-5467 (1998).
Yao et al., "Aptamer-based piezoelectric quartz crystal microbalance biosensor array for the quantification of IgE," Biosensors and Bioelectronics 24:2499-2503 (2009).
Yeung et al., "A DNA biochip for on-the-spot multiplexed pathogen identification," Nucleic Acids Res., 34(18):e118 (2006).
Yu et al., "Preparation of monolithic polymers with controlled porous properties for microfluidic chip applications using photoinitiated free-radical polymerization," Journal of Polymer Science Part A—Polymer Chemistry, 40(6):755-169 (2002).
Zhang et al., "Differentiation and detection of PDGF isomers and their receptors by tunable aptamer capillary electrophoresis," Analytical Chemistry, 81(18):7795-7800.
Zhang et al., "In-vitro selection of bacteriophage Π 29 prohead RNA aptamers for prohead binding," The Journal of Biological Chemistry 273(5):2947-2953 (1998).
Zhao et al., "A MEMS viscometric sensor for continuous glucose monitoring," J. Micromech. Microeng. 17:2528-2537 (2007).
U.S. Appl. No. 15/492,656 (US 2017/0283859), filed Apr. 20, 2017 (Oct. 5, 2017).
U.S. Appl. No. 14/221,596, Jul. 21, 2017 Response to Non-Final Office Action.
U.S. Appl. No. 14/223,767, Sep. 21, 2017 Notice of Abandonment.
U.S. Appl. No. 14/743,303, Oct. 5, 2017 Response to Non-Final Office Action.
U.S. Appl. No. 14/978,716, Aug. 29, 2017 Final Office Action.
U.S. Appl. No. 15/269,494, Nov. 2, 2017 Response to Restriction Requirement.
U.S. Appl. No. 15/269,494, Sep. 13, 2017 Restriction Requirement.
International Search Report dated Jan. 28, 2016 in International Application No. PCT/US15/57086.
Written Opinion of the International Searching Authority for PCT/US2008/057433 dated Sep. 3, 2008
U.S. Appl. No. 15/269,494, Dec. 11, 2018 Non-Final Office Action.
U.S. Appl. No. 15/269,494, Sep. 6, 2018 Amendment and Request for Continued Examination (RCE).
U.S. Appl. No. 15/269,494, Jun. 6, 2018 Final Office Action.
U.S. Appl. No. 15/269,494, Apr. 19, 2018 Response to Non-Final Office Action.
U.S. Appl. No. 15/269,494, Jan. 22, 2018 Non-Final Office Action.
U.S. Appl. No. 14/743,303, Jul. 27, 2018 Notice of Abandonment.
U.S. Appl. No. 14/743,303, Nov. 24, 2017 Final Office Action.
Inokuchi, et al., "Micro Magnetic Separator for Stem Cell Sorting System," Proceedings of the 22nd sensor symposium, Oct. 20-21, 2005, Tokyo, pp. 125-128.

\* cited by examiner

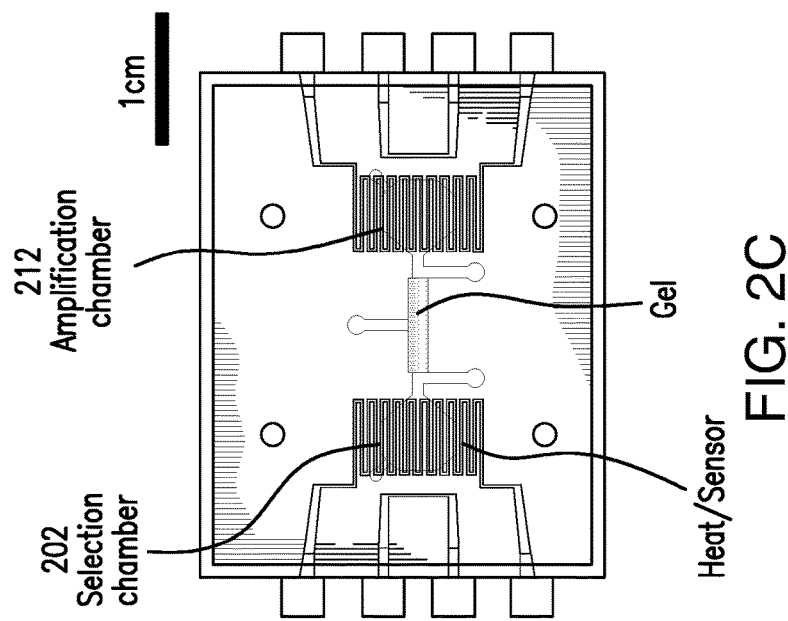
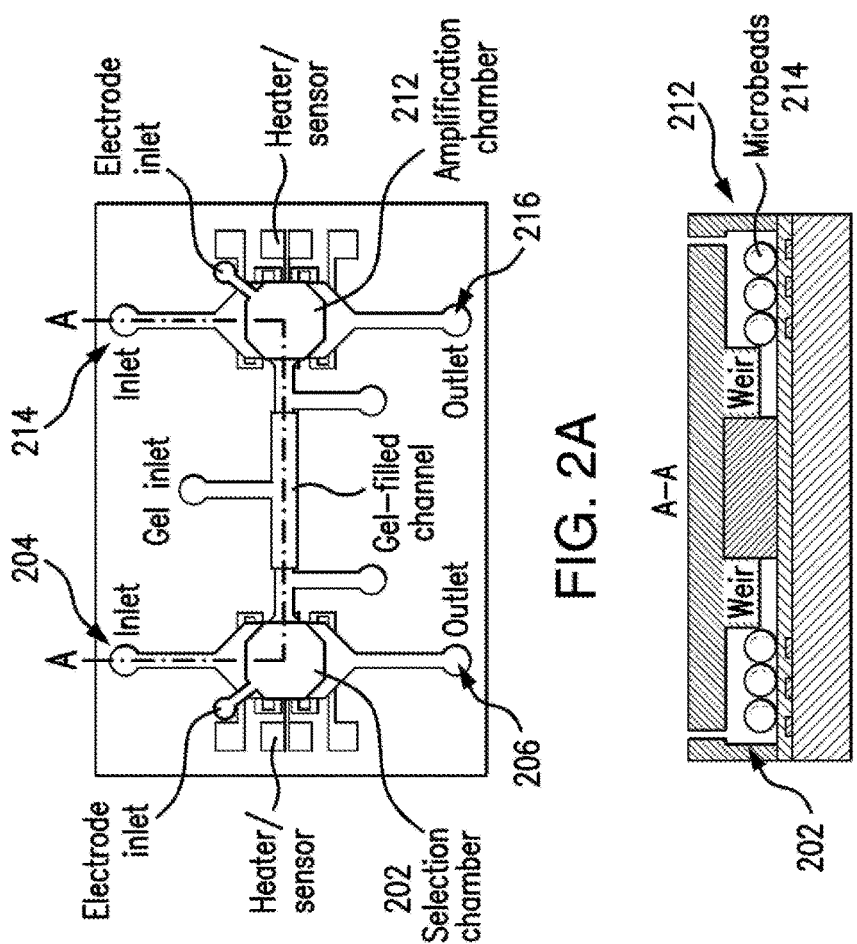

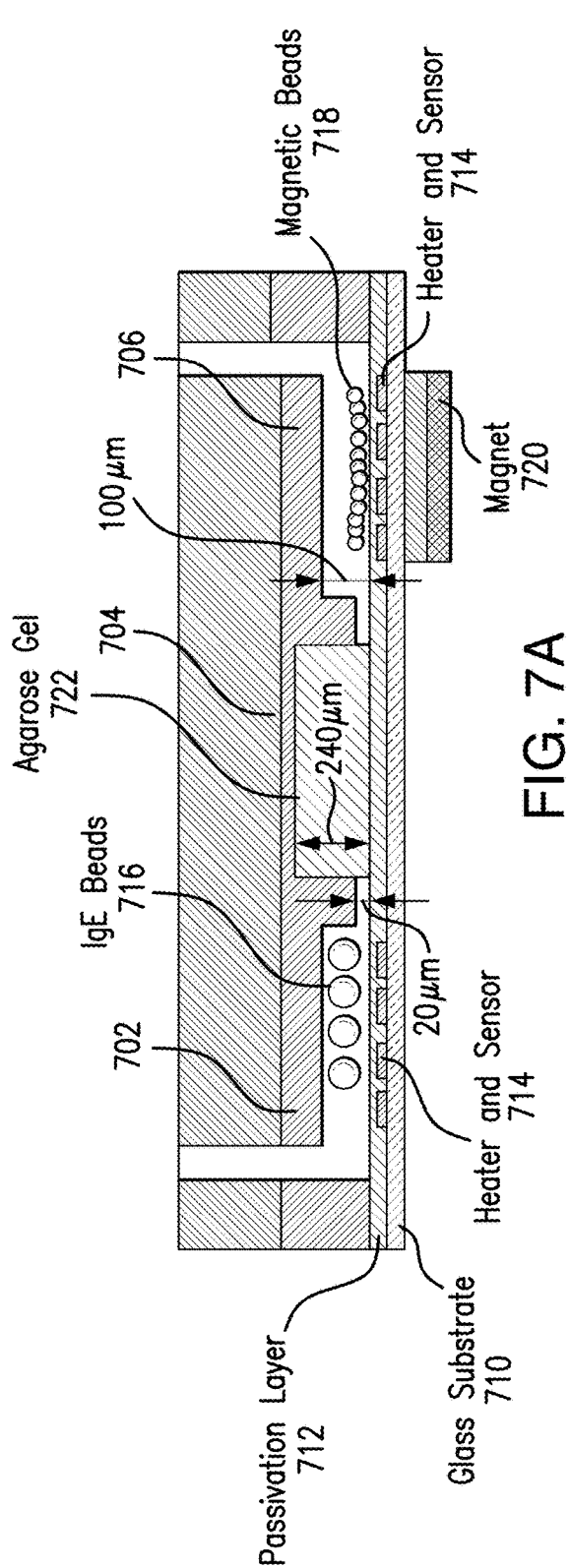
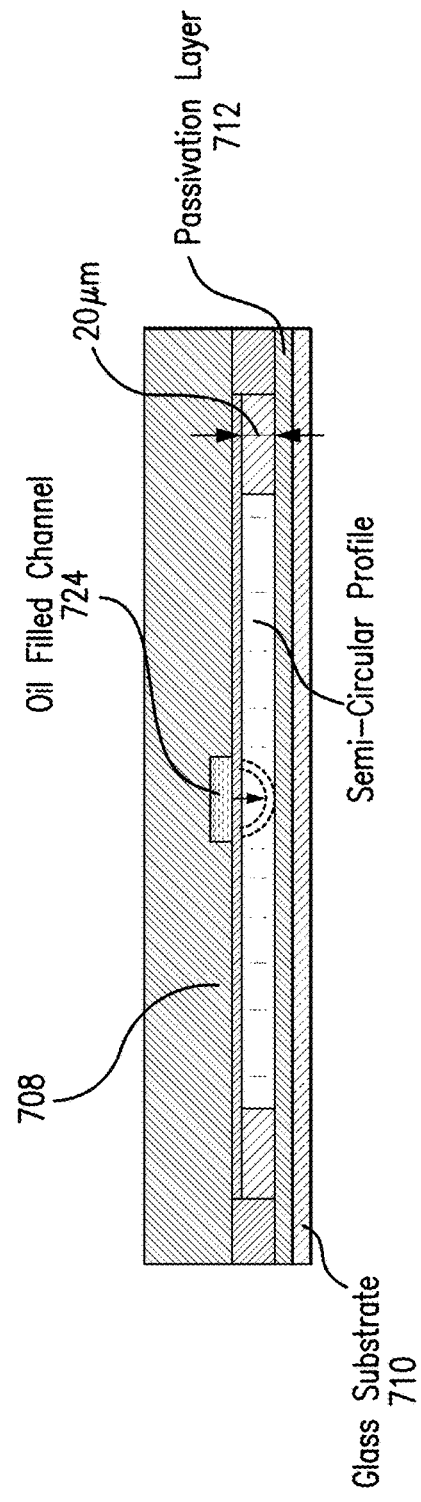
FIG. 7A
FIG. 7B

Affinity of aptamer candidates against 10A IgE protein, and 10B MCF-7 cells.

METHOD OF ISOLATING APTAMERS FOR MINIMAL RESIDUAL DISEASE DETECTION

CROSS REFERENCES TO RELATED APPLICATION

This application is a continuation of International Application No. PCT/US2015/043824, filed Aug. 5, 2015, which claims priority from U.S. Provisional Application No. 62/033,574, filed on Aug. 5, 2014, each of which is incorporated herein by reference in its entirety and priority to each of which is claimed.

STATEMENT REGARDING FEDERALLY FUNDED RESEARCH

This invention was made with government support under CBET-0854030 awarded by the National Science Foundation; RR025816 and CA147925 awarded by the National Institutes of Health. The government has certain rights in the invention.

BACKGROUND

The disclosed subject matter provides techniques for detection of minimal residual disease (MRD), such as in multiple myeloma. Multiple myeloma (MM) accounts for approximately 1.3% of all types of cancer. Certain drug regimen and stem-cell transplantation have improved survival, with a current three-year survival rate at 56.6%. A goal of treatment is to obtain complete response (CR), defined as the absence of monoclonal protein by immunofixation and less than 5% plasma cells in bone marrow (BM). Of patients who obtain CR, those who are negative in minimal residual disease (MRD) in their bone marrow by flow cytometry have better survival than those who are MRD positive. Identification and measurement of MRD can be used in MM care for selecting and guiding therapeutic strategies.

Methods for MRD detection can be based on evaluation of plasma cells obtained from bone marrow aspirates, including multiparameter flow cytometry (MFC) that can detect one clonal cell in $10^4$ normal cells, allele specific polymerase chain reaction (ASO-PCR) that involves sequencing the rearranged variable region (VDJ), and deep sequencing that amplifies RNA with locus-specific primers followed by sequencing. Limitations can include, for example, the poor survival of plasma cells in the specimen that can cause failure of MRD detection, and/or the invasiveness of the procedure that prohibits frequent monitoring.

Methods that are sensitive, specific, non-invasive, and amenable to standardization can be of interest for MRD detection. Serum-based methods can be used, but certain protein electrophoresis (SPEP), immunofixation (IFE) and free light chain ratio (FLC) techniques can be low in sensitivity with limits of detection (LOD) of 500-2000 mg/L (SPEP), 100-150 mg/L (IFE) and up to 1 mg/L (FLC), respectively. Aptamers, single-strand oligonucleotides (oligomers) that bind to targets with high specificity and affinity, can be attractive receptors capable of allowing highly sensitive assays. Certain aptamers have been used to detect proteins in serum, including immunoglobulins with LOD below 2.5 µg/L. These sensitivities are orders of magnitude higher than those of certain serum-based M-Ig detection methods such as SPEP, IFE and FLC.

Apatamers can be obtained from randomized oligomer libraries via an in vitro process termed systematic evolution of ligands by exponential enrichment (SELEX). Since aptamers are isolated from randomized oligomer libraries through an in vitro process termed systematic evolution of ligands by exponential enrichment (SELEX), they can be advantageous over antibodies for analyte detection because they: (1) can be synthetically developed (rather than via immunization of animals) for a target, (2) are amenable to rapid manufacture with minimal batch-to-batch variability, (3) offer controlled selectivity by removing oligomers that bind to counter targets (counter selection) and that nonspecifically bind to the target support (negative selection), and (4) can be designed to bind to particular functional domains of a target (to differentiate targets that differ only minimally) and to possess environmental (e.g., temperature or pH) responsive-ness (for use in sensitive assays).

SUMMARY

The disclosed subject matter provides techniques for selecting and isolating aptamers that target M-Ig proteins with a microdevice including at least a first selection chamber. An illustrative method includes placing a first sample of M-Ig in the first selection chamber and introducing a first group of oligomers including at least an M-Ig targeting oligomer into the first selection chamber, such that the M-Ig targeting oligomer binds to the first sample of M-Ig proteins. The method can also include removing unbound oligomers of the first sample from the first selection chamber to isolate the M-Ig targeting oligomer.

According to another embodiment, the disclosed subject matter provides techniques for selecting and isolating aptamers that target M-Ig proteins. An illustrative method includes providing a microdevice to select and isolate M-Ig targeting oligomers, where the microdevice includes a first selection chamber for positive selection. The method can also include preparing a first sample of M-Ig proteins from a serum, placing the first sample of M-Ig proteins in the first selection chamber; and introducing a first group of oligomers including at least an M-Ig targeting oligomer into the first selection chamber, such that the M-Ig targeting oligomer binds to the first sample of M-Ig proteins. The method can also include removing unbound oligomers of the first sample from the first selection chamber to isolate the M-Ig targeting oligomer.

According to yet another embodiment, the disclosed subject matter provides techniques for selecting and isolating aptamers that target M-Ig proteins. An illustrative method includes providing a microdevice to select and isolate M-Ig targeting oligomers, where the microdevice includes a first selection chamber for positive selection, a second selection chamber for counter-selection, and a third selection chamber for negative selection, where the first selection chamber, the second selection chamber, and the third selection chamber are fluidly coupled to each other. The microdevice can also include an amplification chamber, and a channel, where the channel fluidly couples at least one of the first chamber, second chamber and third chamber with the amplification chamber.

In some arrangements, the method can further include preparing a first sample of M-Ig proteins from a serum, placing the first sample of M-Ig proteins in the first selection chamber, placing a second sample of M-Ig proteins having a heavy and light chain substantially similar to the first sample of M-Ig proteins in the second selection chamber; placing bare beads in the third selection chamber, and introducing a first group of an oligomer including at least an M-Ig targeting oligomer into the first selection chamber, such that the M-Ig targeting oligomer binds to the first sample of M-Ig proteins. The method can also include removing unbound oligomers from the first selection chamber to isolate the M-Ig targeting oligomer.

In some arrangements, the method can also include transferring the M-Ig targeting oligomer to the second selection chamber, such that an unbound oligomer is counter-selected. The method can further include transferring the counter-selected unbound oligomer to the third selection chamber, such that a subsequent unbound oligomer is negatively selected from the counter-selected unbound oligomer. The method can also include transferring the subsequent unbound M-Ig targeting oligomer to the amplification chamber by the channel, and amplifying the M-Ig targeting oligomer in the amplification chamber by polymerase chain reaction.

The disclosed subject matter can be used in the detection of multiple myeloma. In one aspect, the disclosed subject matter provides systems and methods for generating specific idiotype-targeting aptamers. In another aspect, the disclosed subject matter provides aptameric biosensors using idiotype-targeting aptamers and methods for detecting biomarkers using such biosensors.

The disclosed subject matter can produce aptamers with high affinity due to intimate molecular interactions in microscale geometries. Application of microfluidics to aptamer isolation can involve implementing affinity selection against targets immobilized on silica capillary walls, microbeads or sol-gels on microchips, as further discussed herein. Aiming to enable fully integrated and automated isolation of aptamers in a rapid manner and at low cost, the disclosed subject matter provides a microfluidic SELEX approach that can use fully closed-loop microfluidic affinity selection and bead-based PCR amplification of aptamer candidates. Microfluidic SELEX devices as disclosed herein can isolate idiotype-targeting DNA aptamers using serum samples of individual patients. The resulting idiotype-targeting DNA aptamers can be used to construct assays for sensitive and specific detection of M-Ig proteins to enable personalized MRD monitoring.

BRIEF DESCRIPTION OF THE DRAWINGS

The subject matter of the application will be more readily understood from the following detailed description when read in conjunction with the accompanying drawings, in which:

FIG. 2A is a schematic plan view of a microfluidic device for aptamer isolation in which target-binding DNA oligomers were transferred electrokinetically between the selection and amplification microchambers, in accordance with the disclosed subject matter.

FIG. 2B is a cross-sectional view of the microfluidic device of FIG. 2A along line A-A, in accordance with the disclosed subject matter.

FIG. 2C is a plan view of a microfluidic device for aptamer isolation, in accordance with the disclosed subject matter.

FIGS. 7A-7B are cross-section view of the microfluidic device of FIG. 6 in accordance with the disclosed subject matter, wherein FIG. 7A shows a cross-section view along the line a-a and FIG. 7B shows a cross-section view along the line b-b.

FIG. 9A and FIG. 9B show a microfluidic SELEX: gel electrophoresis of selection washes ($W_1$-$W_{10}$) and eluted final-round PCR product (E), wherein FIG. 9A depicts IgE, with the final-round PCR product counter selected against IgG before elution, and FIG. 9B depicts MCF-7 cells, in accordance with the disclosed subject matter.

DETAILED DESCRIPTION

The disclosed subject matter provides techniques for detection of minimal residual disease (MRD), such as in multiple myeloma. As further discussed herein, aptamers have be developed that target M-Ig proteins by using a device. The device uses at least one chamber that assists in isolating an M-Ig targeting oligomer. The chamber can include microbeads that aid in the isolation. The M-Ig targeting oligomer can be mixed with serum from a patient to identify whether minimal residual disease, such as in multiple myeloma, is present in the serum.

Figure 1:
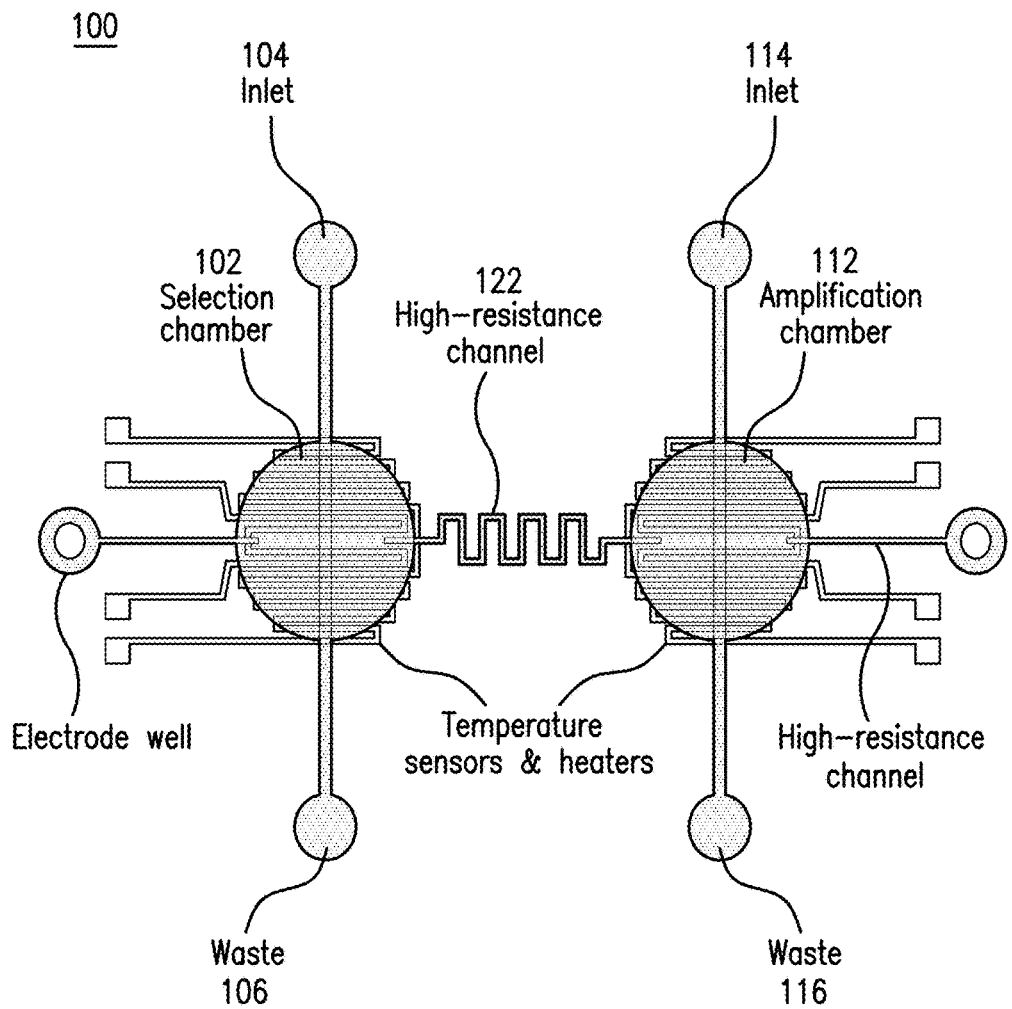
FIG. 1 is a schematic of the optimized microfluidic SELEX device, in accordance with the disclosed subject matter.

In accordance with one embodiment, the disclosed device can be a microfluidic device. The device can include a selection chamber and an amplification chamber, as shown in FIG. 1. The chambers can be, for example, microchambers. Target-binding oligomers can be affinity selected against surface-immobilized proteins such as the M-Ig protein in the selection chamber. The target-binding oligomers can then be transferred to the amplification chamber. In the amplification chamber, the target-binding oligomers can be amplified via polymerase chain reaction (PCR). The product of the amplification can be transferred back to the selection chamber for further affinity selection. The process can be repeated to obtain high-affinity oligomers.

In accordance with one embodiment of the disclosed subject matter, targets and oligomers can be manipulated in microchambers using magnetic bead-based immobilization of target molecules and oligomers. The microfluidic device can also include resistive heater devices and temperature sensors beneath the chambers for environmental control and thermal cycling, as further discussed herein.

In accordance with one embodiment of the disclosed subject matter, the selection chamber can be connected to the amplification chamber via a high-resistance channel. The channel can be serpentine-shaped. Transfer of oligomers between the selection chamber and the amplification chamber can be accomplished using, for example, electrophoresis. High-resistance microchannels can also be used to connect electrode wells to the chambers. The high-resistance channels can inhibit cross contamination between the channels. The high-resistance channels can also inhibit the transfer of electrolytically generated species from the electrodes. The serpentine channel can also inhibit thermally induced failures of gels.

In accordance with certain embodiments of the disclosed subject matter, on-chip monitoring of the amplification and selection processes can be used. For example, on-chip monitoring of SELEX progress can be performed using qPCR (quantitative PCR). In accordance with certain embodiments of the disclosed subject matter, the microfluidic device can enable rapid development of aptamers specifically targeting tumor-specific biomarkers in serum samples of individual patients (e.g., multiple myeloma patients) to provide personalized, sensitive, and noninvasive MRD detection.

In accordance with another aspect of the disclosed subject matter, systematic evolution of ligands by exponential enrichment (SELEX) can be used in the detection of MRD. Serum samples can be drawn from a patient and protein samples, such as M-Ig samples, can be prepared. The samples can be prepared, for example, by using gel electrophoresis followed by isoelectric focusing.

The patient protein samples can then be used to isolate idiotype-targeting DNA aptamers. The protein samples can be incubated with magnetic beads. For example, M-Ig samples can be incubated with magnetic beads that contain NHS groups. The beads can then be washed, and a buffer added to the solution, to quench any unreacted NHS groups.

A SELEX procedure can then be performed. In accordance with one embodiment, the SELEX procedure can be performed using protein samples for two or more different patients of the same or substantially similar heavy and light chain type. However, in other embodiments protein samples for only a single patient can be used. Bead suspensions can be introduced into a SELEX device such as a microfluidic SELEX device as disclosed herein. Several rounds of SELEX can be performed, such as, but not limited to, three rounds.

Aptamer candidate ssDNA can be eluted from the device. The ssDNA can be further amplified by off-chip PCR and purified to remove excess PCR reagents and primers. The aptamers can then be sequenced. The aptamers can be used to develop assays performed in laboratories or point-of-care instruments to detect proteins such as M-Ig proteins, allowing for personalized monitoring of MRD. Protein samples can be obtained from the patient and the assays can be used to detect MRD within the sample. In accordance with one embodiment, patient-specific aptamers generated in accordance with the disclosed subject matter can be used in aptameric biosensors. For example, patient-specific aptamers can used in aptameric biosensors for highly sensitive and specific multiple myeloma residual disease detecting assays. Detection of minimal residual disease can be important to multiple myeloma care.

In accordance with one embodiment, the disclosed subject matter can include optimizing a microfluidic device for reliable and rapid isolation of aptamers. FIG. 1 depicts an exemplary microfluidic aptamer selection device 100, which is further discussed below. As discussed in detail below, target-binding oligomers are affinity selected against surface-immobilized M-Ig protein in the selection microchamber 102 and transferred to the amplification microchamber 112 for amplification via PCR. Both the selection chamber 102 and the amplification chamber 112 can respectively include an inlet 104, 114 and an outlet 106, 116 for waste. The product from the amplification microchamber 112 is transferred back to the selection chamber 102 for further affinity selection. This process can be repeated to obtain high-affinity oligomers (aptamers) to the protein. Reagent handling in the individual chambers can be via flow driven by a pressure source. The transfer of oligomers between the chambers can be via electrophoresis through a serpentine-shaped channel 122 of high resistance to flow and diffusion. The device can reliably integrate the SELEX process and rapidly (e.g., within one day) perform iterative rounds of affinity selection and amplification of target-binding DNA oligonucleotides from a randomized library to isolate aptamers specific to immunoglobulin proteins. In accordance with another embodiment, the disclosed subject matter can include obtaining and testing aptamers that bind to M-Ig prepared from individual patient sera. The M-Ig protein samples can be prepared from sera of individual patients via gel electrophoresis and isoelectric focusing, and these samples can be used in the optimized microfluidic SELEX device to isolate idiotype-targeting aptamers. The specificity and affinity of the resulting aptamers can also be tested. In accordance with one embodiment, the disclosed systems and methods can be used for detection of multiple myeloma.

Microchips for multi-round SELEX isolate aptamers against targets including small molecules, proteins and cells. The chips can be fabricated via soft lithography. The chips can include a plurality of chambers. As shown in FIGS. 2A-2C, two chambers or microchambers are provided, respectively for affinity selection and amplification of target-binding oligomers. However, any number of chambers are contemplated herein. FIG. 2A depicts a selection chamber 202 and an amplification chamber 212. Both the selection chamber 202 and the amplification chamber 212 can respectively include an inlet 204, 214 and an outlet 206, 216. FIG. 2B is a cross-sectional view of the microfluidic device of FIG. 2A along line A-A that includes microbeads 214 therein. FIG. 2C is a plan view of a microfluidic device for aptamer isolation, in accordance with the disclosed subject matter.

The selection and amplification chambers can include a plurality of suitable sub-devices for further processing and optimization. For example, the chambers of FIG. 2A are each integrated with micro heater devices 208 and temperature sensors 210 for closed-loop temperature control. Reagent handling within each chamber can be via pressure-driven fluid flow although other methods of handling are contemplated herein. Oligomers are transferred between the chambers via a plurality of suitable methods, such as but not limited to pressure-driven flow or electrophoresis through a microchannel filled with a DNA-permeable gel, as shown in FIG. 2.

Figure 4:
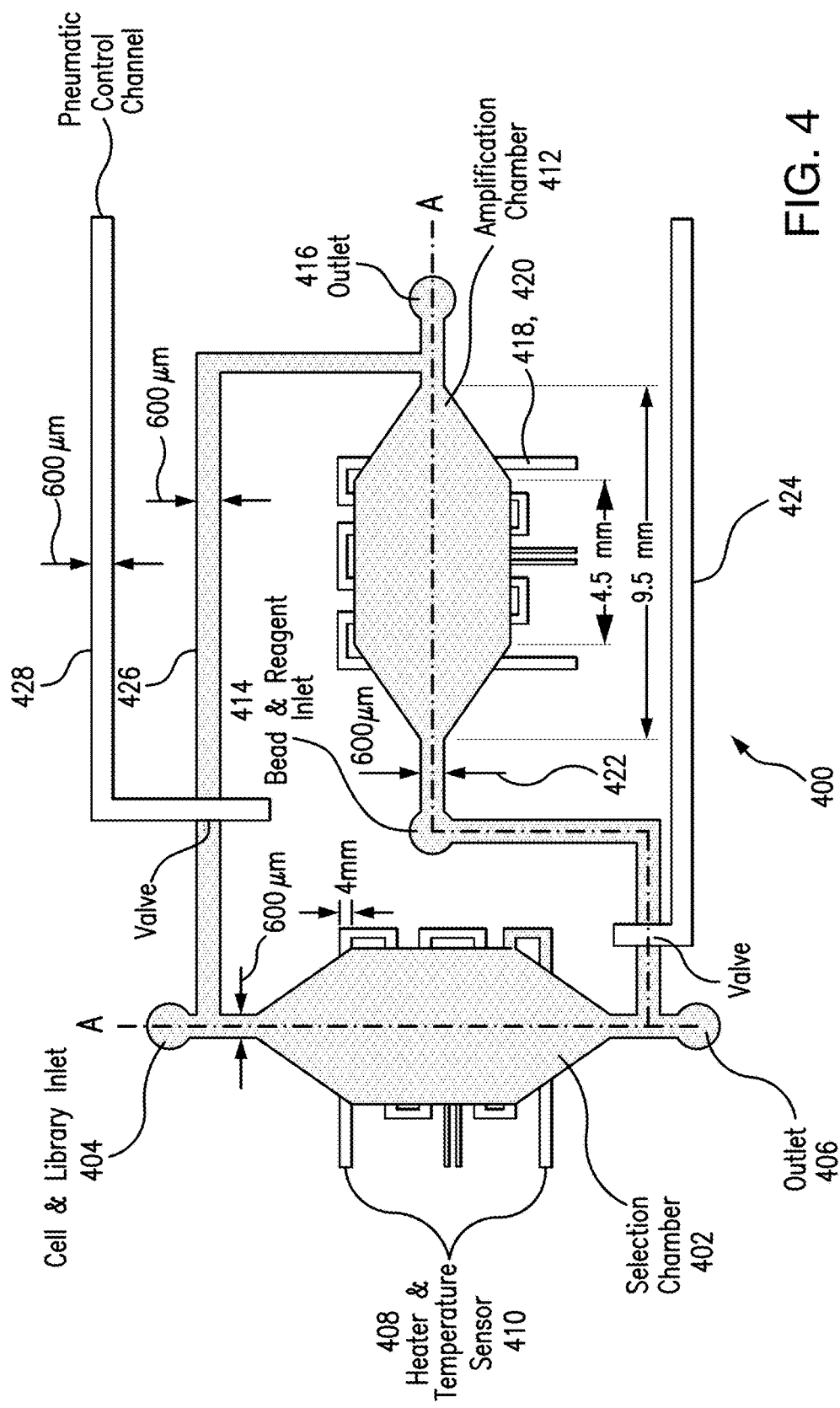
FIG. 4 is a top view of an exemplary embodiment of a microfluidic device for aptamer development in accordance with the disclosed subject matter.

An exemplary embodiment of a microdevice 400 in accordance with the disclosed subject matter is illustrated in FIG. 4. As shown in FIG. 4, the microdevice 400 can include a selection chamber 402. The selection chamber can be fabricated using standard microfabrication techniques, e.g., using polydimethylsiloxane (PDMS) soft lithography to create a chamber with desired shape and dimension. For example and not limitation, the selection chamber 402 can have a semi-circular profile with a height of about 20 µm. The selection chamber can include an inlet 404 to permit introduction of samples. For example, a random ssDNA library can be introduced via the inlet 404 at the start of a systematic evolution of ligands by exponential enrichment (SELEX) process. The microdevice 400 can also include an outlet 406 to permit for disposal of waste materials. For example, the non-M-Ig-targeting oligomers can be removed via the outlet 406 during washing.

The microdevice 400 can further include a heater device, such as a microheater, 408 and a temperature sensor 410. The microheater 408 can be a resistive heater and can be formed in a serpentine shape, although any suitable shape is contemplated herein. The temperature sensor 410 can be a resistive temperature sensor can be formed in a serpentine shape. The heater device 408 and temperature sensor 410 can be used to control the temperature in the selection chamber 402 using, for example, electronic control circuitry.

The microdevice 400 can further include an amplification chamber 412. The amplification chamber 412 can include an inlet 414 and an outlet 416, and the temperature of the amplification chamber 412 can be controlled by a heater device 418 and temperature sensor 420, as described in connection with the selection chamber 402. The selection chamber 402 and the amplification chamber 412 can be coupled via a channel, such as a first microchannel 422. The first microchannel 422 can include one or more microvalves configured to hydrodynamically transfer oligomers from the selection chamber 402 to the amplification chamber 412 or can utilize other methods of transfer as further described herein. In the embodiment of FIG. 4, the one or more microvalves can be actuated by a first pneumatic control channel 424. The first pneumatic control channel 442 can be filled with any suitable substance, such as but not limited to, water and oil.

The one or more microvalves in first microchannel 422 can further be configured to hydrodynamically transfer oligomers from the amplification chamber 412 to the selection chamber 402. Alternatively or additionally, a second microchannel 426 between the selection chamber 402 and the amplification chamber 412 can be used. The second microchannel 426 can include one or more microvalves configured to hydrodynamically transfer oligomers from the amplification chamber 412 to the selection chamber 402 or can utilize other methods of transfer as further described herein. The one or more microvalves in second microchannel 426 can be actuated by a second pneumatic control channel 428.

Figure 5:
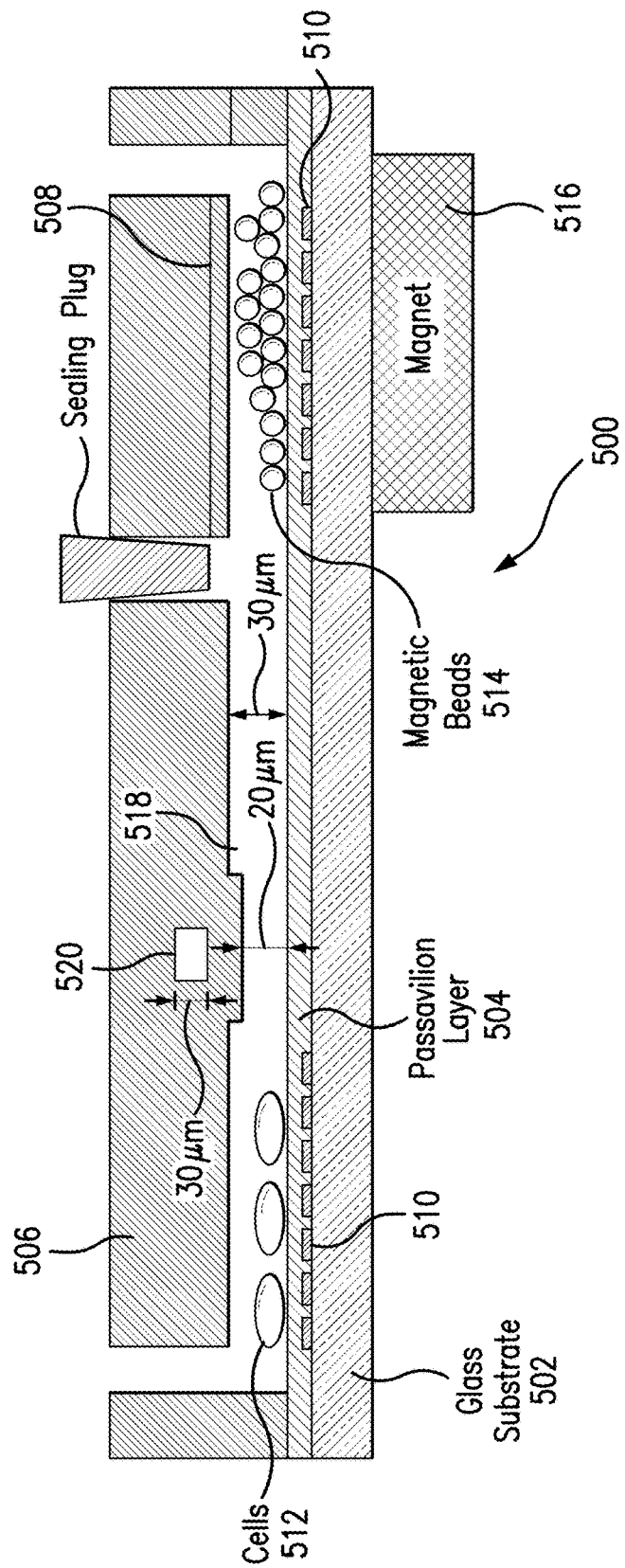
FIG. 5 is a cross-sectional view of the microfluidic device of FIG. 4 along line a-a in accordance with the disclosed subject matter.

FIG. 5 illustrates a cross-sectional view of a microdevice 500 in accordance with an exemplary embodiment of the disclosed subject matter. The microdevice includes a substrate 502 such as a glass substrate. A passivation layer 504 can be situated between the substrate and the interior of the selection chamber 506 and the amplification chamber 508. Temperature control elements 510, including microheater devices and temperature sensors, can be situated within the passivation layer beneath each of the selection chamber 506 and the amplification chamber 508.

The amplification chamber can include primer-functionalized microbeads such as magnetic beads 514. The magnetic beads 514 can be, for example, streptavidin-coated polymer beads. The magnetic beads 514 can be held in place by an external magnet 516 positioned below the amplification chamber 508.

A microchannel 518 can connect the selection chamber 506 to the amplification chamber 508. One or more microvalves, which are not shown in FIG. 6, can be configured to hydrodynamically transfer oligomers between the selection chamber 506 and the amplification chamber 508 or can utilize other methods of transfer as further described herein. The one or more microvalves can be actuated by a pneumatic control channel 520.

Figure 6:
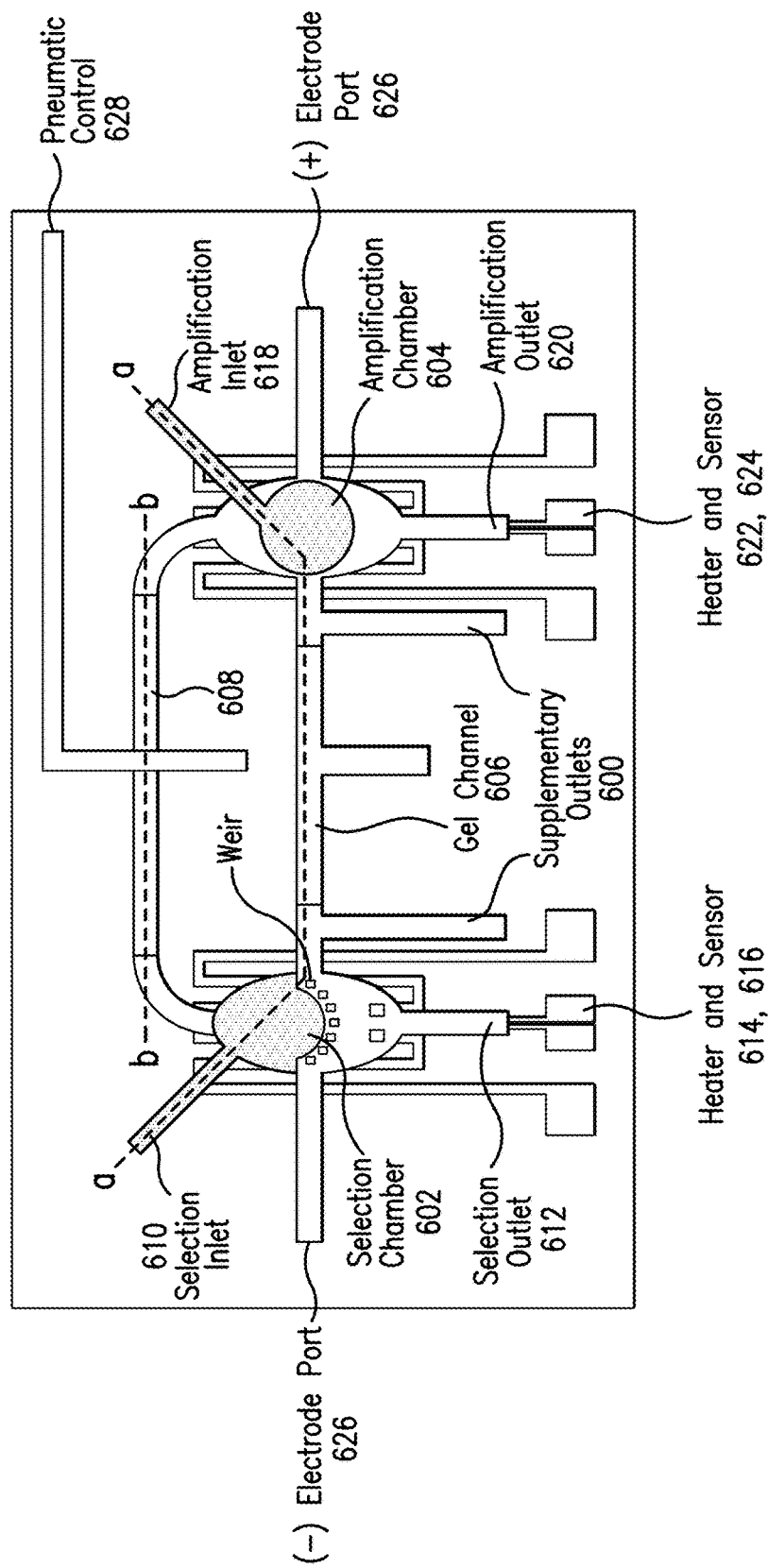
FIG. 6 is a top view of another embodiment of a microfluidic device for aptamer development in accordance with the disclosed subject matter.

In another aspect, the disclosed subject matter provides a microdevice for isolating and amplifying an aptamer. An exemplary embodiment of a microdevice 600 in accordance with the disclosed subject matter is illustrated in FIG. 6. The microdevice can include a selection chamber 602, an amplification chamber 604, a first microchannel 606 and a second microchannel 608 according to this embodiment. The first microchannel is located between the selection chamber 602 and the amplification chamber 604 and is configured to transfer oligomers from the selection chamber 602 to the amplification chamber 604. The second microchannel can be located between the selection chamber 602 and the amplification chamber 604 and is configured to transfer oligomers from the amplification chamber 604 to the selection chamber 602. At least one of the first microchannel and the second microchannel includes one or more microvalves configured to hydrodynamically transfer oligomers. In accordance with another embodiment of the disclosed subject matter, the microdevice can include only a single microchannel configured to transfer oligomers in both directions, as shown in FIG. 2.

The selection chamber 602 and the amplification chamber 604 can be fabricated using standard microfabrication techniques as noted above, e.g., using PDMS soft lithography to create chambers with desired shape and dimension. For example and not limitation, the selection chamber 602 can have a semi-circular profile with a height of about 20 µm.

The microdevice 600 can include a selection chamber inlet 610 and a selection chamber outlet 612 for introduction and disposal of sample materials. For example, a randomized ssDNA library can be introduced via selection chamber inlet 610, while unbound and weakly bound ssDNA can be removed via the selection chamber outlet by washing. The microdevice can also include a selection chamber heater 614 and a selection chamber temperature sensor 616. The heater 614, which can be a resistive heater and be formed in a serpentine shape, and the temperature sensor 616, which can be a resistive sensor and be formed in a serpentine shape, can be located below the selection chamber 602 and can be used to control the temperature within the selection chamber 602. The microdevice can similarly include an amplification chamber inlet 618, an amplification chamber 620, an amplification chamber heater 622, and an amplification chamber temperature sensor 624.

As shown in FIG. 6, the first microchannel 606 can be configured to transfer oligomers via electrophoresis. For example, the first microchannel 606 can be filled with a gel such as but not limited to agarose gel. The agarose gel can allow electrokinetically driven ssDNA migration while preventing bulk flow. First and second electrode ports 626 can be provided on opposite ends of the first microchannel 606.

The first and second electrode ports 626 can be configured to receive wires such as platinum wires. The platinum wires can be coupled to an electrical circuit for generating an electric field across the first microchannel 606.

In accordance with another embodiment of the disclosed subject matter, the first microchannel 606 can be configured to hydrodynamically transfer oligomers from the selection chamber to the amplification chamber or can utilize other methods of transfer as further described herein. The first microchannel can include one or more microvalves configured to hydrodynamically transfer aptamers from the selection chamber to the amplification chamber. The one or more microvalves can be actuated by a first pneumatic control channel. The first pneumatic control channel can be filled with any suitable substance, such as but not limited to, water and oil.

The second microchannel 608 can be configured to hydrodynamically transfer aptamers from the amplification chamber to the selection chamber or can utilize other methods of transfer as further described herein. For example, the second microchannel can include one or more microvalves configured to hydrodynamically transfer oligomers from the amplification chamber 604 to the selection chamber 602. The one or more microvalves can be actuated by a pneumatic control channel 628.

FIGS. 7A-7B illustrate cross-sectional views of a microdevice 700 in accordance with an exemplary embodiment of the disclosed subject matter. FIG. 7A shows a cross-sectional view of microdevice 700 of FIG. 6 along the line a-a including a selection chamber 702, a first microchannel 704, and an amplification chamber 706. FIG. 7 shows a cross-sectional view of microdevice 700 of FIG. 6 along the line b-b including a second microchannel 708.

The microdevice 700 can include a substrate 710 such as a glass substrate. A passivation layer 712 can be situated between the substrate 710 an the interior of the selection chamber 702 and the amplification chamber 704. Temperature control elements 714 can be positioned below each of the selection chamber 702 and the amplification chamber 704.

The selection chamber 702 can include immobilized targets 716. For example, the immobilized targets 716 can be Immunoglobin E-functionalized microbeads, as shown in FIG. 7A. In accordance with other embodiments of the disclosed subject matter, the immobilized targets 716 can be, metal ions, small molecules, peptides, amino acids, proteins, viruses, and bacteria.

The amplification chamber 704 can include primer-functionalized microbeads 718. The primer-functionalized microbeads 718 can be magnetic beads such as, for example, polymer beads coated with streptavidin. The magnetic beads can be held in the amplification chamber 704 by a magnet such as an external magnet 720 positioned below the amplification chamber 704.

The first microchannel 706 can be configured to transfer oligomers from the selection chamber 702 to the amplification chamber 704 via electrophoresis. For example, as shown in FIG. 7A, the first microchannel 706 can be filled with a gel such as but not limited to agarose gel 722. In accordance with another embodiment of the disclosed subject matter, the first microchannel 706 can be configured to hydrodynamically transfer oligomers from the selection chamber to the amplification chamber or can utilize other methods of transfer as further described herein. The first microchannel can include one or more microvalves configured to hydrodynamically transfer oligomers from the selection chamber to the amplification chamber. The one or more microvalves can be actuated by a first pneumatic control channel. The first pneumatic control channel can be filled with any suitable substance, such as but not limited to, water and oil.

With reference to FIG. 7B, the second microchannel 708 can be configured to hydrodynamically transfer oligomers from the amplification chamber 704 to the selection chamber 702 or can utilize other methods of transfer as further described herein. For example, the second microchannel 708 can include one or more microvalves configured to hydrodynamically transfer oligomers from the amplification chamber 704 to the selection chamber 702. The one or more microvalves can be actuated by a pneumatic control channel 724. The pneumatic control channel 724 can be located in a PDMS layer above the second microchannel 708.

In accordance with the disclosed subject matter, microfluidic bead-based amplification is conducted in the amplification chamber. As such, PCR on microbeads can be performed in the chamber with an integrated heater and temperature sensor, as described above. For a given single-strand DNA (ssDNA) template, the reverse primer can be attached to microbeads, such as agarose microbeads or magnetic microbeads having a mean diameter of 80 µm, via dual biotin-streptavidin coupling, while the solution-borne forward primer can be conjugated with a fluorophore (carboxyfluorescein), thus allowing fluorescent detection of bead-bound PCR product. As such, optimal reaction parameters that maximize template amplification and minimize spurious amplification can be investigated.

Figure 3:
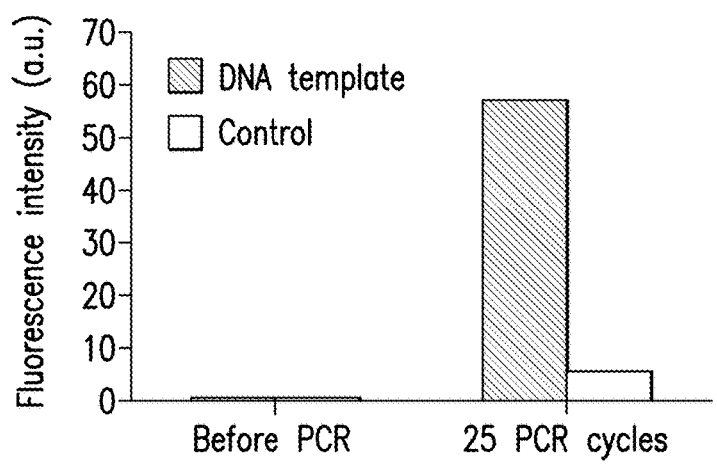
FIG. 3 is a bar chart showing mircofluidic bead-based PCR: fluorescence from bead-bound PCR product of an 87-nt random SSDNA strand, in accordance with the disclosed subject matter.

In one example according to the disclosed subject matter, micro-fluidic bead-based PCR of a 181-bp segment of the *B. pertussis* genome can be optimized with an $MgCl_2$ concentration of 1.5 mM, an annealing temperature of approximately 58° C., a dwell time of approximately 20 s, and a bead concentration of approximately 200 beads/µL. The optimal $MgCl_2$ concentration and annealing temperature are consistent with findings from conventional solution based PCR. The optimal dwell time, attributable to miniaturization-enabled rapid and uniform sample heating, is considerably shorter than those (approximately 60 sec) for conventional bead-based PCR platforms and consistent with microchip solution-based PCR results. The optimal bead concentration reflects a tradeoff between available surface area and steric effects that respectively support and hinder the reaction. Using these parameters and as shown in FIG. 3, microfluidic bead-based PCR also showed effective amplification of templates from randomized libraries to be used in SELEX.

Figure 8:
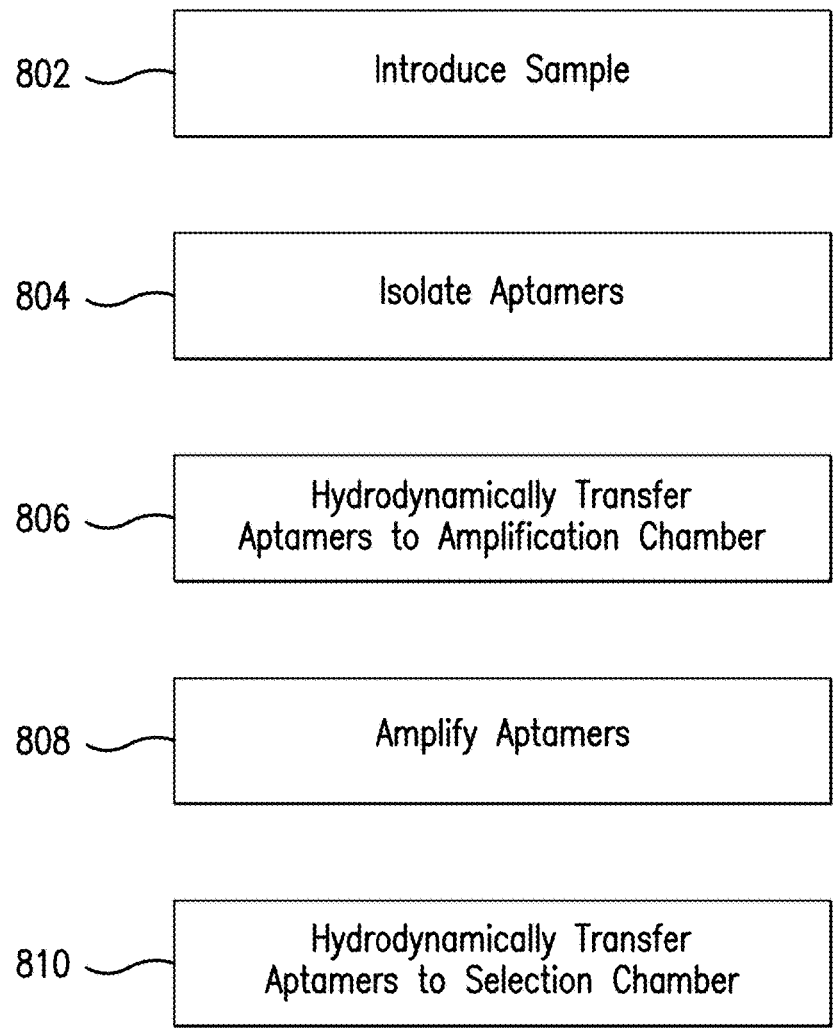
FIG. 8 is a flowchart of another exemplary embodiment of a method for isolating and amplifying aptamers in accordance with the disclosed subject matter.

In yet another aspect and with reference to FIG. 8, the disclosed subject matter provides a method for isolating and amplifying an aptamer, including introducing a first sample comprising oligomers into a selection chamber at 802. The first sample can be, for example, a randomized ssDNA library. The selection chamber can include an immobilized target. In accordance with an embodiment, the immobilized target can include functionalized microbeads. The microbeads can be retained in the selection chamber by a weir structure. In accordance with further embodiments, the immobilized target can be immobilized metal ions, small molecules, peptides, amino acids, proteins, viruses, or bacteria.

The oligomers can then be isolated at 804. For example, the oligomers can be allowed to strongly bind with an immobilized target. The unbound and weakly bound ssDNA can then be removed by washing, e.g., using a washing buffer such as Dulbecco's Phosphate-Buffered Saline (D-PBS). The oligomers can then be eluted in preparation for transfer to the amplification chamber, as known in the art. In accordance with an exemplary embodiment of the disclosed subject matter, the oligomers can be thermally eluted. For example, the temperature of the selection chamber can be raised using on-chip microheater devices and temperature sensors. In accordance with another embodiment, the oligomers can be chemically eluted.

With further reference to FIG. 8, the aptamer can be transferred from the selection chamber to the amplification chamber via a first microchannel at 806. In accordance with an exemplary embodiment of the disclosed subject matter, the oligomers can be hydrodynamically transferred from the selection chamber to the amplification chamber via the first microchannel or can utilize other methods of transfer as further described herein. The oligomers can be transferred using one or more microvalves. The microvalves can be, for example, elastomeric microvalves. For example, the microvalves can be constructed using SU-8. The microvalves can be actuated by a pneumatic control channel. For example, the pneumatic control channel can be a pressure-driven, oil-filled channel. The channel can be located above the microchannel between the selection chamber and the amplification channel. In accordance with other embodiments of the disclosed subject matter, the oligomers can be transferred from the selection chamber to the amplification chamber by electrophoresis.

After the oligomers are transferred from the selection chamber to the amplification chamber, the immobilized target can be removed from the selection chamber. The selection chamber can be washed, e.g., using a buffer, and a new batch of immobilized targets can be loaded in the selection chamber.

The oligomers can be amplified in the amplification chamber at 808. The amplification chamber can include primer-functionalized microbeads. For example, the primer-functionalized microbeads can be magnetic beads such as polymer beads coated with streptavidin, which is known to have extraordinarily high affinity for biotin. The primer (e.g., a reverse primer) can be biotin-functionalized and immobilized onto the surface of the beads. The magnetic beads can be held in the amplification chamber by an external magnet. For example, the magnet can be placed below a bottom portion of the amplification chamber. When the sample including the oligomer is introduced into the amplification chamber (e.g., via the first microchannel), the oligomers can hybridize to the bead-immobilized primers and/or reverse primers due to molecular recognition (e.g., Watson-Crick type base pairing). Other molecules in the sample, such as molecules, cells, small molecules, and the like, are less likely to bind with the primers.

A polymerase chain reaction (PCR) technique can be applied to amplify the oligomers. Using the bead-immobilized primer and PCR reagents (including e.g., Taq polymerase, deoxynucleotide triphosphates, and buffer), a complementary DNA can be produced based on the target DNA, which together with the target DNA forms a double-stranded DNA (ds-DNA) tethered on the beads. Such ds-DNA can be denatured (or melted) at an elevated temperature, e.g., about 95° C., to separate the target DNA from the complementary DNA. A second primer, e.g., a forward primer, can be annealed onto the complementary DNA (e.g., at the free end of the complementary DNA) at a lowered temperature, e.g., at 50-62° C. Thereafter, using the complementary DNA as a template, the second primer, and the PCR reagents, another copy of the target DNA can be produced, at a suitable chain extension temperature, e.g., about 72° C. Repeating the above temperature cycles (melting, annealing, and extension) can result in amplification of the target DNA, i.e., generation of exponentially increasing duplicate copies of the target DNA.

The untethered second primer can be labeled with a spectroscopically detectable tag (e.g., a fluorophore). In such a case, the result of the amplification after a number of PCR cycles can be fluorophore-labeled target DNA and unlabeled, bead-tethered complementary strands. Such labeled target DNA can be isolated for detection by fluorescent spectroscopy.

With further reference to FIG. 8, the oligomers can be hydrodynamically transferred from the amplification chamber to the selection chamber at 810 or can utilize other methods of transfer as further described herein. For example, the single strand can be released from the bead bound single strand by heating the selection chamber 810 can be heated to 95° C. and/or by using chemical methods such as NaOH. In accordance with an exemplary embodiment of the disclosed subject matter, the oligomers can be hydrodynamically transferred from the selection chamber to the amplification chamber via a second microchannel. In another embodiment of the disclosed subject matter, the oligomers can be hydrodynamically transferred from the selection chamber to the amplification chamber via the first microchannel or can utilize other methods of transfer as further described herein, as shown in FIG. 2. The oligomers can be transferred using one or more microvalves. The microvalves can be, for example, elastomeric microvalves. For example, the microvalves can be constructed using SU-8. The microvalves can be actuated by a pneumatic control channel. For example, the pneumatic control channel can be a pressure-driven, oil-filled channel. The channel can be located above the microchannel between the selection chamber and the amplification channel. In embodiments where the oligomers can be transferred from the amplification chamber to the selection chamber using the first microchannel, the microvalves can be configured to be bi-directional.

After the oligomers are transferred to the selection chamber, the used streptavidin beads can be removed from the amplification chamber. In accordance with certain embodiments of the disclosed subject matter, the external magnet can be removed and/or turned off. New streptavidin beads can be introduced into the amplification chamber and held in place (e.g., by replacing and/or turning on the external magnet). In accordance with certain embodiments of the disclosed subject matter, the selection and amplification process can be repeated one or more additional times.

As depicted in FIG. 2A, preliminary multi-round SELEX of DNA aptamers in microchips can be performed. Binding ssDNA oligomers are selected by incubating a randomized library (72-nt) with proteins attached to agarose beads (mean diameter: 90 μm) in the selection chamber. Alternatively, cells can be utilized instead of the proteins that can be trapped by a microweir in the selection chamber, as shown in FIG. 2B. Non-binding oligomers are removed via (e.g. ten) buffer washes ($W_1$-$W_{10}$), which are collected for later offline analysis. Although 10 buffer washes are shown, any number of suitable washes are contemplated herein. Binding oligomers are released thermally or chemically, transferred by pressure-driven flow or electrophoresis into the amplification chamber, captured by primer-functionalized agarose beads, and amplified via PCR (18/22-nt forward/reverse primers). The amplified DNA binders (after washing) were thermally released from beads, and transferred back to the selection chamber. This process can be repeated for multiple rounds until the SELEX process is terminated.

Figure 9A:
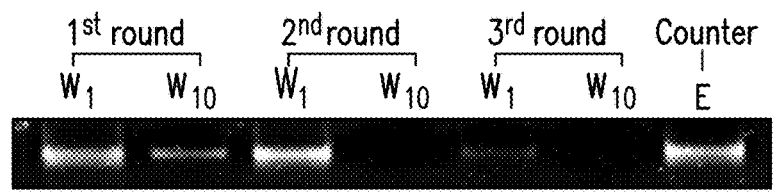
Figure 9B:
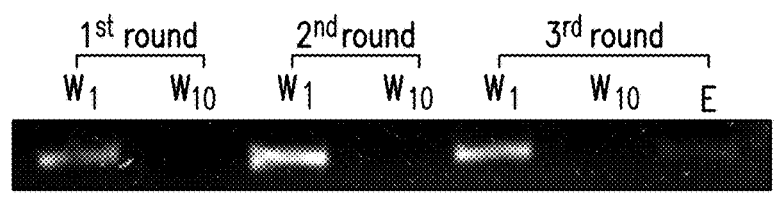

As shown in FIGS. 9A and 9B, aptamer candidates are thus obtained (e.g., via electrokinetic oligomer transfer) for the human immunoglobulin E (IgE) protein (See FIG. 9A) and MCF-7 breast cancer cell line (See FIG. 9B) in three SELEX rounds (first round, second round, and third round) and eluted final-round PCR product (E). The gel electrophoresis of selection washes ($W_1$-$W_{10}$) show decreasing fluorescence within each round as weakly binding oligomers are removed. For IgE as represented in FIG. 9A, the PCR product at the end of the third round is transferred back into the selection chamber, where it is counter-selected against bead-immobilized immunoglobulin G (IgG) as a counter target, and the non-binding oligomers are collected and the binding oligomers are left behind. Fluorescence observed in the eluent (E) indicates isolation of strongly IgE-binding aptamer candidates. Similar results are obtained for MCF-7 cells as shown in FIG. 9B, for which the SELEX process is terminated following affinity selection in the final ($3^{rd}$) round. Although the example of FIG. 9A and FIG. 9B includes three rounds, any number of rounds are contemplated herein.

Figure 10A:
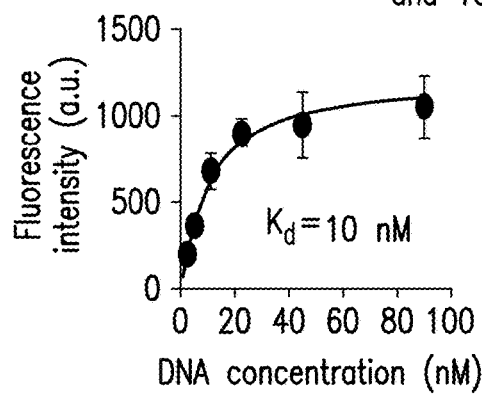
FIG. 10A is a line graph of the affinity of aptamer candidates against IgE protein, in accordance with the disclosed subject matter.
Figure 10B:
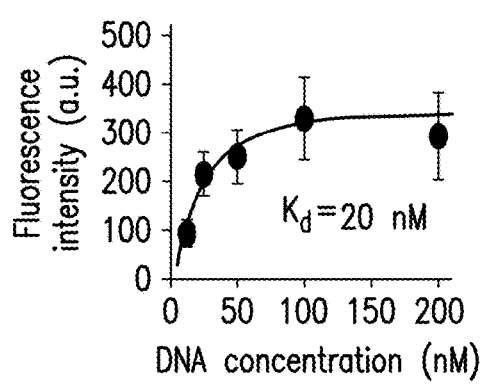
FIG. 10B is a line graph of the affinity of aptamer candidates against MCF-7 cells, in accordance with the disclosed subject matter.

The specificity and affinity of the aptamer candidates can be tested. For example, fluorescently labeled strands of a sequence from the IgE aptamer candidate pool can be incubated with IgE- or IgG-functionalized beads. By fluorescent measurement of bead-bound strands, the strands are shown not to bind to IgG, while binding strongly to IgE, with an equilibrium dissociation constant of $K_d$=10 nM that compares favorably with that of known anti-IgE aptamers (10-35 nM), as shown in FIG. 10A. The affinity of aptamer candidates for MCF-7 cells is analyzed using suitable methods, such as flow cytometry for measurement of the average fluorescence intensity of cells, as shown in FIG. 10B. This yielded $K_d$=20 nM, which was for the first time obtained for MCF-7 aptamers, and comparable to $K_d$ of aptamers for other cancer cells.

In accordance with an exemplary embodiment of the disclosed subject matter, the microfluidic SELEX device as described above can be further optimized for rapid isolation of aptamers against M-Ig proteins in individual patient sera, and the specificity and affinity of the resulting aptamers can be tested. As noted above, the microfluidic SELEX device can be used to isolate aptamers against M-Ig proteins. The microfluidic SELEX device can have dimensions and characteristics as set forth in Table 1 below, for certain optimal applications of the device, such as isolating against M-Ig proteins.

TABLE 1

Estimated dimensions and characteristics for the optimized microfluidic SELEX device.

| Parameter | Value |
| --- | --- |
| Microchambers | 3.2 mm diameter × 125 μm (1 μL) |
| EK transfer channel | 10 mm × (25 × 5 μm$^2$) (1.25 nL) |
| Inlet & outlet channels | 2 mm × (250 × 125 μm$^2$) (6.25 nL) |
| Inlets and outlets | 1 mm (diameter) |
| Overall device footprint | 20 × 10 mm$^2$ |
| EK channel flow resistance | 732 kPa/(μL/min) |
| Outlet channel flow resistance | 4.1 × 10$^{-4}$ kPa/(μL/min) |
| EK/Outlet channel flowrate ratio | 5.6 × 10$^{-7}$ (i.e., negligible) |
| Concentration change rate in chambers via diffusive mixing | 45 ppm/hr (i.e., negligible) |
| EK channel electric field & voltage | 25 V/cm and ~25 V |
| EK velocity & transport time | 1.5 mm/min and 6.7 min |

The device can be fabricated of the elastomer polydimethylsiloxane (PDMS) on a glass substrate via soft lithography. The device can be capable of performing (within one day) iterative rounds of affinity selection and amplification of target-binding DNA oligomers from a randomized library to isolate aptamers with specific affinity to M-Ig.

As noted above, the optimized device can include a selection chamber and an amplification chamber. The device can also include microchannels of high resistance to bulk fluid flow and diffusion to connect the chambers, as well as connect the electrode wells to the chambers. These channels can prevent cross contamination between the chambers and keep electrolytically generated species at the electrodes away from the chambers, while allowing effective electrokinetic migration of DNA oligomers between the chambers. Also, magnetic micro-beads can be used to provide support for protein targets and DNA primers to facilitate their manipulation.

Affinity selection of target-binding oligomers, including positive, counter and negative selection, can be performed from a randomized DNA library in the selection chamber. The microchamber (1 μL, Table 1) can be integrated with a microheater device and temperature sensor. The selection chamber can contain magnetic microbeads, which are functionalized with the target protein (i.e., for positive selection) or a counter target (i.e., for counter selection), or have no molecular coating (i.e., for negative selection). The beads can be held in place by an external magnet device and can be mixed with the surrounding fluid via magnet-driven motion.

During selection processes, the amplification chamber can be used as an auxiliary chamber (for temporary storage of oligomers between the positive, counter and negative selection procedures) and can contain magnetic bead-immobilized short ssDNA probes complementary to the 3' end of library strands. Between the chambers, oligomers can be electrokinetically transferred (velocity: ~1.5 mm/min, channel traversal time: ~6.7 min; electric field: 25 V/cm, voltage between the electrodes: ~25 V as given in Table 1) through a channel, such as but not limited to a serpentine-shaped channel have an approximate length dimension of 10 mm, with high resistance to bulk fluid flow (less than a millionth of flow in the outlet channel) and to diffusion (rate of concentration change in the chambers due to diffusion-induced mixing through the channel: ~45 ppm/hr). Within each chamber, reagents (targets, beads and buffers) are loaded or removed via fluid flow driven, such as but not limited to, by a pressure source at the inlet to the chamber (with other inlets and outlets closed as needed).

Figures 11A, 11B, 11C:
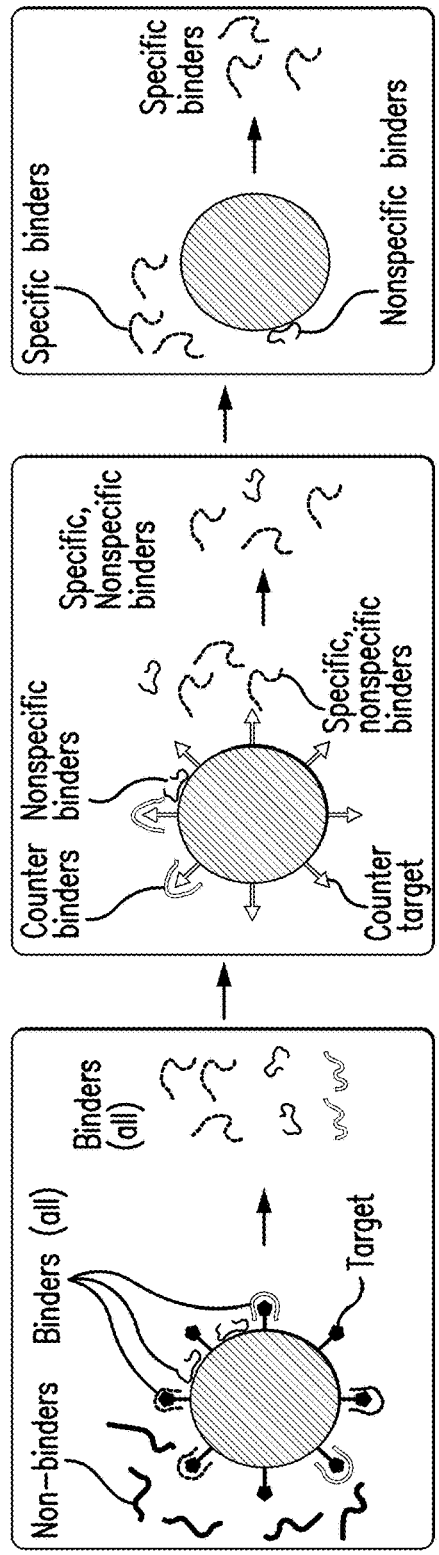
FIG. 11A shows affinity selection against a target for positive selection: binding oligomers are selected via capture by the bead-immobilized target, in accordance with the disclosed subject matter.
FIG. 11B shows affinity selection against a target for counter selection: binders to a bead-tethered counter target are captured and eliminated, in accordance with the disclosed subject matter.
FIG. 11C shows affinity selection against a target for molecule-targeting aptamers, nonspecific binders adsorb to bare beads while specific binders are eluted, in accordance with the disclosed subject matter.

Affinity selection can start with positive selection as represented in FIG. 11A such that target-binding oligomers are captured by the bead-based target, purified, released thermally or chemically, and transferred electrokinetically (through the serpentine channel) into the amplification chamber, where they are captured onto beads by ssDNA probes. Next, counter selection processes can be conducted as represented in FIG. 11B such that the selection chamber is replenished with a bead-immobilized counter target; the oligomers stored in the amplification chamber are released from immobilized probes by denaturation, and transferred electrokinetically back into the selection chamber. Undesired binders are captured by the counter targets for elimination, leaving desired binders in solution. Next, as represented by FIG. 11C, negative selection processes are performed similar to counter selection, except that the selection chamber contains bare beads to eliminate nonspecific binders by surface adsorption.

The affinity selection process can be performed under prescribed environmental conditions (e.g., at approximately 37° C.) to produce aptamers with optimized binding properties. Aptamers with such prespecified temperature-dependent binding characteristics can allow easy molecular manipulation in sensitive assays for detection of the protein target.

Affinity selection can be characterized using a model DNA library constructed by spiking randomized ssDNA strands with a known aptamer at different concentrations. The ssDNA solution can be incubated with the target (e.g. IgE) (or counter target, e.g. IgG and immunoglobulin M (IgM)) in a microchamber and then eluted for analysis by off-chip PCR followed by gel electrophoresis as in the studies noted above. The results can show the presence (or absence) of the known aptamer in the case of successful selection (or counter selection). Using these experiments, affinity selection can be optimized using different designs of on-chip heater devices and temperature sensors, and different schemes of magnetic bead functionalization and immobilization including the size, surface coating, molecular immobilization density, and concentration of beads as well as the choice and manipulation of the external magnet.

Target-binding oligomers obtained in affinity selection can be transferred electrokinetically into the amplification chamber, and amplified therein via bead-based PCR. The chip as shown in FIG. 1 can be used to investigate the use of magnetic beads with thermally stable primer functionalization for more efficient automation, incorporating high-resistance serpentine channels for more efficient and reliable electrokinetic oligomer transfer, and realizing on-chip monitoring of PCR status and on-chip assessment of PCR product affinity.

Figure 12A:
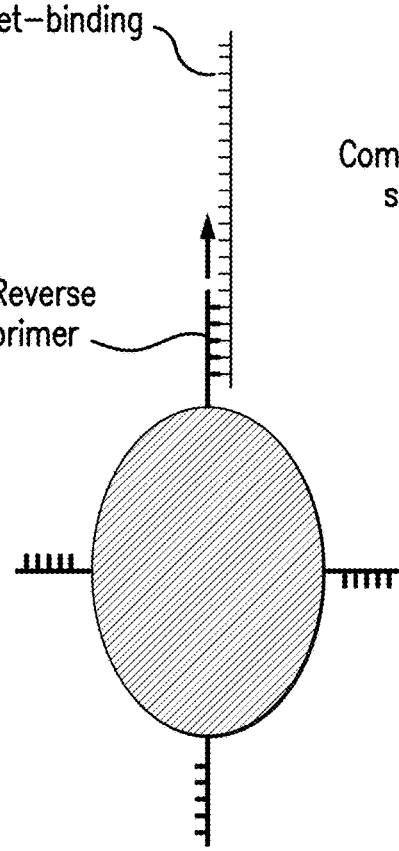
FIG. 12A shows bead-based PCR for a target-binding strand (template) hybridizes onto the bead-immobilized reverse primer, in accordance with the disclosed subject matter.
Figure 12B:
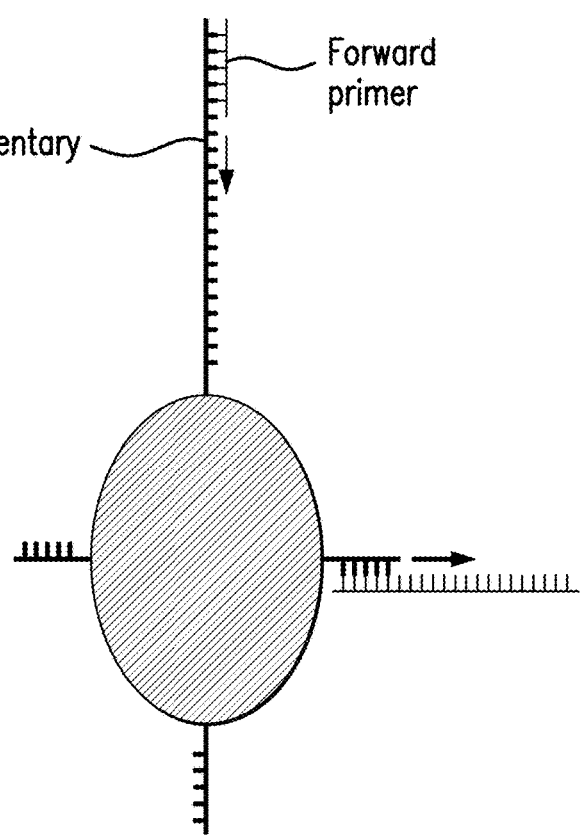
FIG. 12B shows the reverse primer is extended into a complementary strand, which is used in the next cycle to produce a copy of the template, in accordance with the disclosed subject matter.

The target-binding oligomer amplification uses the same temperature control, fluid handling and electrokinetic transport methods as in affinity selection described herein. Template ssDNA (target-binding DNA) is captured by a reverse primer attached to magnetic microbeads via a dual biotin-streptavidin link (which has been preliminarily determined to be sufficiently stable at elevated temperatures required by PCR) or if needed, via covalent surface attachment (e.g., carbodiimide coupling) as shown in FIG. 12A. Thermal cycling can produce a bead-tethered complimentary strand hybridized to a duplicate copy of the template, as shown in FIG. 12B. This process is repeated until the beads are saturated with double-stranded DNA (dsDNA), which is purified by rinsing and then denatured to release the duplicate template copies (amplified target-binding DNA) into solution for the next SELEX round.

To inform when to end PCR within each round of SELEX, on-chip monitoring of PCR status can be enabled via quantitative PCR (qPCR). The fluorescent dye SYBR Green (excitation/emission: 497/520 nm) can be allowed to intercalate within the bead-immobilized dsDNA product, which can hence be fluorescently quantified. On-chip assessment of PCR product affinity to monitor SELEX progress. The affinity of the PCR product to the target can be estimated for (later) on-chip monitoring of the SELEX iteration progress. Using a Cy5-labeled (excitation/emission: 650/670 nm, compatible with SYBR Green) forward primer can result in Cy5-labled duplicate copies of the template, whose total amount is indicated by SYBR Green fluorescence intensity ($I_{SG}$) from the last qPCR cycle (noted above). These strands are transferred and bind to target protein-functionalized beads freshly loaded in the selection chamber. After washing away weak binders, Cy5 fluorescence ($I_{Cy5}$) of target-bound oligomers is measured. The normalized fluorescence ($I_{Cy5}/I_{SG}$) represents the fraction of PCR-amplified oligomers that bind more strongly to the target and is used as a measure of the affinity of the PCR product.

Microfluidic PCR on magnetic beads can be characterized using a known DNA aptamer as template. PCR can be run through a varying number of cycles, with the product monitored in real time on-chip and also analyzed off-chip using standard procedures. The effects of (1) chip surface coating, (2) magnetic bead size, concentration, surface coating, and primer functionalization chemistry and density, and (3) different microheater and temperature sensor designs can be determined. For example, having shown that the chip materials (glass and PDMS, either unmodified or coated with Parylene or treated with bovine serum albumin) are largely compatible with PCR, surface coatings (e.g., poly (ethylene glycol) or poly(ethylene oxide)), as well as commercially available PCR-compatible magnetic microbeads (e.g., Dynabeads), can be further investigated to minimize nonspecific adsorption. The optimal amplification and specificity (i.e., minimized spurious amplification) and the required number of thermal cycles (expected to be in the range 15-20 from the preliminary data) can be assessed, benchmarked against prior related work (solution-based microfluidic PCR and conventional bead-based PCR).

Affinity selection and amplification can be integrated to enable optimal microfluidic isolation of aptamers, as described above with respect to FIG. 1. Similar to the individual selection and amplification modules, reagents can be handled within each chamber via pressure-driven flow, and target-binding oligomers transferred between the chambers via electrophoresis (under a voltage bias at the appropriate electrodes) in the high-resistance serpentine channel. Closed-loop temperature control can be accomplished using integrated micro temperature sensors and heaters (or external heaters if needed). In the initial SELEX round, a randomized ssDNA oligomer library undergoes positive, counter and negative selection in the selection chamber. The resulting target-binding oligomers are transferred to the amplification chamber, captured by primer-functionalized magnetic beads, and amplified with on-chip status monitoring. The amplified binders are purified, released from beads, and transferred back into the selection chamber for selection of stronger binders, whose affinity is estimated via the normalized Cy5 fluorescence intensity. SELEX then proceeds with a new round or is terminated as appropriate.

The functionality of the microfluidic SELEX device can be verified using an established immunoglobulin (e.g., IgE). First, the capture efficiency of electrophoresed oligomers by microbeads can be studied due to its importance to the system integration. Fluorescently labeled oligomers can be electrokinetically transferred from the selection chamber through the serpentine channel to primer-functionalized beads in the amplification chamber. Strands captured on beads can be quantified to assess the capture efficiency. The appropriate transfer time can be verified, as well as pH and salt concentrations of the buffer for oligomer capture. Next, the integrated device can be tested using the model ssDNA library to verify its capability for microfluidic SELEX against established targets. The normalized Cy5 fluorescence (and hence the affinity of aptamer candidates being enriched from the library) is expected to increase with the number of SELEX rounds, achieving saturation within about 5 rounds according to our preliminary studies. The resulting aptamer candidates are also expected to be target-specific by showing poor affinity to counter targets.

M-Ig protein samples can be prepared from sera of individual patients, and these samples can be used to isolate idiotype-targeting aptamers in the microfluidic device. M-Ig protein samples can be prepared from serum of individual patients using a two-stage procedure comprising gel electrophoresis followed by isoelectric focusing. These M-Ig samples can then be used in the microfluidic SELEX device optimized (for example, as described above) to isolate idiotype-targeting aptamers. The resulting aptamers can be tested for their specificity and affinity. For example, the procedure can include first loading serum protein samples into multiple tracks of an agarose gel and that can be run at a constant voltage of approximately 250 V in a flatbed electrophoresis chamber. The run can be stopped when the albumin marker has migrated 4 cm from the application point. One track of the electropherogram can be excised and stained to detect clonally-restricted gamma-bands indicative of monoclonal immunoglobulin. The excised and stained track can then be used as a template for locating these bands in the other tracks while a scalpel blade can be used to isolate the bands of interest. The isolated segments can then be frozen overnight at approximately −20° C., thawed and placed in the barrel of a 3 mL plastic syringe fitted with a 21 G needle, forced through the syringe, and collected in a tube. The tube, now containing agarose paste, can be centrifuged at approximately 78,000 g for approximately 10 min and the clarified supernatant can be recovered.

The recovered solution can then be subject to isoelectric focusing at approximately pH 3-10 to further discriminate and enrich the monoclonal immunoglobulin from potential polyclonal contaminates. Focusing can proceed at a constant power (~10 W) until pI markers are stabilized and show optimal separation. Again, one track of the focused gel can be excised and stained to identify the location of the monoclonal immunoglobulin. This track can then be used for the identification and isolation of the monoclonal region of the other bands. These fragments can be frozen, agitated and centrifuged as described above. The immunoglobulin recovered can be measured by nephelometry. To verify this immunoglobulin extraction process, a sample from the resulting protein can be retested in agarose gel electrophoresis to confirm the presence of a single monoclonal immunoglobulin band. The remaining immunoglobulin solution can be stored indefinitely at approximately −20° C. This gel extraction process can require some time for processing, such as about two days, with most of the time devoted to gel freezing.

This method can recover up to approximately 70% of monoclonal protein; and in gel electrophoresis of M-Ig proteins, which is by definition highly abundant in serum, the recovered M-Ig protein can have a purity of approximately 99% or greater. It is anticipated that less than approximately 1 mL of serum can be collected to obtain approximately 30 μg of protein needed for microfluidic SELEX, and approximately 20 μg of protein needed for microfluidic affinity and specificity testing.

This method may not be appropriate for cases, as such, in accordance with another embodiment, in certain circumstances (e.g., where the monoclonal immunoglobulin has migrated out of the gamma region as is often the case for IgA proteins), affinity purification can be performed using an immunoglobulin specific recombinant bacterial binding protein. Columns can be prepared with the immobilized binding protein to which serum will be introduced. The column can be centrifuged and washed, and the bound material can be eluted and collected.

The patient M-Ig samples can obtained can be used to demonstrate rapid isolation of idiotype-targeting DNA aptamers in the microfluidic device. M-Ig protein samples from patients obtained above can be incubated with magnetic beads that contain N-hydroxysuccinimide (NHS) groups. The primary amines (—$NH_2$) which exist at every N-terminus of each polypeptide chain of the immunoglobulin can react with the NHS groups on the bead surface to form stable amide bonds, thereby tethering the immunoglobulin to the magnetic bead surface. Following incubation the beads can be washed and Tris buffer added to the solution to quench unreacted NHS groups.

The protein isolation and immobilization procedure can be executed with protein samples from two different patients of the substantially same heavy and light chain to obtain, respectively, a suspension of bead-bound target monoclonal immunoglobulin for which the aptamer is sought to bind and a suspension of bead-bound counter target monoclonal immunoglobulin. The bead suspensions can be introduced into the microfluidic device where iterative affinity selection with target M-Ig beads, counter selection with counter target M-Ig beads, negative selection with bare beads can be performed, followed by amplification of selected binding oligomers via bead-based PCR. This SELEX process can continue for several rounds (approximately <5 rounds or within one day), which can allow isolation of aptamers of sufficient affinity according to experience.

The pool of aptamer candidate ssDNA can be eluted from the microfluidic device, further amplified by off-chip PCR, and purified to remove excess PCR reagents and primers. A PCR cloning kit, such as manufactured by Qiagen, can then be used to sequence the product. Briefly, purified PCR products can be mixed with a plasmid cloning vector containing a gene in its DNA that confers antibiotic resistance. The DNA of the plasmid can be cleaved with a restriction endonuclease enabling the insertion of the DNA into the vector DNA (i.e., now recombinant DNA) when in the presence of a DNA ligase. The recombinant DNA can be introduced to a host organism, *Escherichia coli* (*E. coli*) bacteria, which can take up the recombinant DNA through transformation. The *E. coli* can be exposed to an antibiotic which allows bacteria that are harboring the recombinant DNA to survive while bacteria that have failed to take up the recombinant DNA will die. The surviving *E. coli* can be plated in an agar medium. The bacteria can form colonies of identical recombinant DNA. Colonies can be isolated and their DNA can be extracted for further analysis.

Specificity and affinity of aptamers can be tested using M-Ig proteins (which can be obtained as described above) from serum samples from the particular patient whose M-Ig the aptamers are expected to bind specifically, and from other patients whose M-Ig the aptamers are expected not to bind.

Microfluidic fluorescent measurements can be used to test affinity and specificity. In a microchamber, fluorescently labeled aptamers (either the entire SELEX-produced pool or select sequences) can be incubated with microbead-immobilized target proteins. Fluorescence from the beads and eluent can then be measured using a microscope and a fluorescence spectrometer, respectively. By performing the incubation under appropriate environmental conditions (e.g. temperature and pH), this process can also allow investigation of the environmental dependence of the aptamer-target binding. To obtain data allowing comparison of our aptamers to those in the literature for established proteins (for validation of the device before testing it on M-Ig proteins), affinity and specificity measurements can be performed using off-chip methods such as surface plasmon resonance (SPR). Data analysis using Langmuir's isotherm can allow determination of the equilibrium dissociation constant ($K_d$) and binding stoichiometry, while measurements against counter targets can allow assessment of the binding specificity.

The disclosed subject matter can be used to rapidly isolate aptamers using serum from individual patients. The entire process of developing such aptamers from patient serum to sequenced DNA aptamers, including preparation of M-Ig protein samples, isolation of aptamer pools targeting M-Ig, testing of the binding affinity and specificity, and obtaining the DNA sequence identity for the aptamers, can be completed in a timely manner, such as for example, within about two weeks or less. The aptamers can then be used in assays performed either in centralized laboratories or point-of-care instruments to sensitively and specifically detect M-Ig proteins, allowing personalized monitoring of MRD. The sensitivity of the testing disclosed herein can be compared with established methods such as protein electrophoresis, immunofixation, bone marrow biopsy and flow cytometry for sensitivity, progression free survival and overall survival.

As such, the disclosed subject matter can address the specific, sensitive and rapid detection of MRD in peripheral blood using personalized aptamers. These aptamers can be highly specific as they are generated against patients' individual and tumor-specific idiotypes isolated from peripheral blood. The innovative microfluidic technology can provide for rapid discovery of aptamers (within a day, compared to one month or longer). Such aptamers can enable personalized and sensitive detection of M-Ig, and hence MRD, in the patients, thereby bringing about potentially transformative improvements in the clinical care of multiple myeloma. Accordingly, the disclosed subject matter can include microfluidic technology.

In particular relevance to MRD detection, aptamers have been used to detect proteins in serum, including immunoglobulins, at sensitivities orders of magnitude higher than those of existing serum-based M-Ig detection methods. Sensitive detection in serum can potentially be achieved by assays using receptors that target the variable region on the M-Ig's light chain. This region, called an idiotype, is tumor-specific and unique to the patient. Such an assay would require development of patient idiotype-binding receptors. To enable sensitive MRD detection, aptamers discussed herein have been developed for individual patients because of the uniqueness of idiotypes to the patient. Highly sensitive MRD detection can be realized using aptamers specific to M-Ig idiotypes in serum of individual patients, as discussed herein. The use of aptamers allows for personalized, highly sensitive monitoring of MRD in multiple myeloma.

As discussed above, aptamers can be rapidly generated that bind to patient-specific and tumor-specific idiotypes of M-Ig proteins found in serum samples of individual patients. The aptamers can then be used in assays that enable detection of MRD with a high sensitivity, in a drop of blood in the physician's office. Rapid aptamer generation can be accomplished using microfluidic technology as discussed above. The disclosed subject matter can isolate immunoglobulin-binding aptamers within approximately 10 hours using preliminary microfluidic devices, and propose to develop personalized idiotype-targeting aptamers for individual patients. Microfluidic devices in accordance with embodiments of the disclosed subject matter can be capable of rapid development of aptamers specifically targeting tumor-specific biomarkers in serum samples of individual patients (e.g., multiple myeloma patients) to enable personalized, sensitive, and noninvasive MRD detection. The resulting aptamers can be used to construct assays that enable sensitive and specific MRD monitoring.

While the disclosed subject matter is described herein in terms of certain embodiments, those skilled in the art will recognize that various modifications and improvements can be made to the disclosed subject matter without departing from the scope thereof. Additional features known in the art likewise can be incorporated, such as disclosed in International Serial No. PCT/US15/22044 entitled, "Methods and Devices for Selection and Isolation of Aptamers," filed Mar. 23, 2015, which is incorporated in its entirety by reference herein. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

The invention claimed is:

1. A method for selecting and isolating aptamers that target M-Ig proteins, comprising:
    a) providing a microdevice to select and isolate M-Ig targeting oligomers comprising:
        a first selection chamber for positive selection,
        a second selection chamber for counter-selection, wherein the first selection chamber is connected to the second chamber via a first channel,
        a third selection chamber for negative selection, wherein the second selection chamber is connected to the third selection chamber via a second channel, and
        an amplification chamber, wherein the amplification chamber is connected to at least one of the first chamber, second chamber, and third chamber via a third channel, wherein the first, second, and third channels are configured to hydrodynamically and/or electrokinetically transfer a solution;
    b) obtaining a first sample of M-Ig proteins from a serum;
    c) placing the first sample of M-Ig proteins in the first selection chamber;
    d) placing a second sample of M-Ig or polyclonal immunoglobulin proteins having a heavy and light chain substantially similar to the first sample of M-Ig proteins in the second selection chamber;
    e) placing beads without a molecular coating in the third selection chamber;
    f) introducing a first group of oligomers including at least an M-Ig targeting oligomer into the first selection chamber, whereby the M-Ig targeting oligomer binds to the first sample of M-Ig proteins;
    g) removing unbound oligomers from the first selection chamber to isolate the M-Ig targeting oligomer;
    h) transferring the M-Ig targeting oligomer to the second selection chamber, whereby an unbound oligomer is counter-selected;
    i) transferring the counter-selected unbound oligomer to the third selection chamber, whereby a subsequent unbound oligomer is negatively selected from the counter-selected unbound oligomer;

j) transferring the subsequent unbound M-Ig targeting oligomer to the amplification chamber through the second channel by a pressure-driven or electrokinetic-driven flow; and k) amplifying the M-Ig targeting oligomer in the amplification chamber by polymerase chain reaction.

2. The method of claim 1, wherein the obtaining of the first sample of M-Ig proteins comprises gel electrophoresis; and isoelectric focusing.

3. The method of claim 1, further comprising purifying the M-Ig proteins using affinity purification after the obtaining of the first sample of M-Ig proteins.

4. The method of claim 3, wherein the affinity purification comprises using a immunoglobulin specific recombinant bacterial binding protein.

5. The method of claim 1, wherein the first selection chamber comprises microbeads functionalized with a target M-Ig protein, wherein the method further comprises immobilizing the first sample of M-Ig proteins on the microbeads in the first selection chamber.

6. The method of claim 5, wherein the microbeads comprise N-hydroxysuccinimde (NHS) groups functionalized magnetic beads to immobilize the M-Ig proteins.

7. The method of claim 1, wherein the amplification chamber comprises primer-functionalized magnetic beads configured to capture the M-Ig targeting oligomer.

8. The method of claim 1, further comprising forming the first selection chamber, the second selection chamber, the third selection chamber, and the amplification chamber on a microchip.

9. The method of claim 8, further comprising hydrodynamically or electrokinetically transferring the M-Ig targeting oligomer from the amplification chamber to the first selection chamber.

* * * * *

UNITED STATES PATENT AND TRADEMARK OFFICE
CERTIFICATE OF CORRECTION

PATENT NO. : 10,294,471 B2  
APPLICATION NO. : 15/414376  
DATED : May 21, 2019  
INVENTOR(S) : Lin et al.

Page 1 of 1

It is certified that error appears in the above-identified patent and that said Letters Patent is hereby corrected as shown below:

In the Specification

In Column 1, Lines 17-21, under the heading, STATEMENT REGARDING FEDERALLY FUNDED RESEARCH:
"This invention was made with government support under CBET-0854030 awarded by the National Science Foundation; RR025816 and CA147925 awarded by the National Institutes of Health. The government has certain rights in the invention."

Should read:
-- This invention was made with government support under grant 0854030 awarded by the NSF and grants CA147925, RR02586, GM104204, and CA196470 awarded by the National Institutes of Health. The government has certain rights in the invention. --

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*